United States Patent
Takehara et al.

(10) Patent No.: US 6,656,130 B2
(45) Date of Patent: Dec. 2, 2003

(54) FEMALE PHYSICAL CONDITION MANAGING APPARATUS

(75) Inventors: Tomoko Takehara, Tokyo (JP); Kazue Sato, Senboku-Machi (JP); Tamaki Shoji, Asaka (JP); Michiko Baba, Shiraoka-Machi (JP)

(73) Assignee: Tanita Corporation, Tokyo (JP)

( * ) Notice: Subject to any disclaimer, the term of this patent is extended or adjusted under 35 U.S.C. 154(b) by 68 days.

(21) Appl. No.: 09/968,035

(22) Filed: Oct. 2, 2001

(65) Prior Publication Data

US 2002/0040195 A1 Apr. 4, 2002

(30) Foreign Application Priority Data

| Oct. 2, 2000 | (JP) | ................................. 2000-302753 |
| Oct. 2, 2000 | (JP) | ................................. 2000-302754 |
| Apr. 26, 2001 | (JP) | ................................. 2001-129937 |

(51) Int. Cl.⁷ .............................................. A61B 10/00
(52) U.S. Cl. ............................................... 600/551
(58) Field of Search ............................. 600/551, 547, 600/591

(56) References Cited

U.S. PATENT DOCUMENTS 5,137,028 A    8/1992   Nishimura 6,402,699 B1 * 6/2002 Kodama et al. ............. 600/551

FOREIGN PATENT DOCUMENTS

| EP | 0498303 A1 | 8/1992 |
| JP | 63-35249 | 7/1988 |
| JP | 04-2254 | 1/1992 |
| JP | 04-72261 | 11/1992 |
| JP | 07-24093 | 6/1995 |
| JP | 10-80426 | 3/1998 |

OTHER PUBLICATIONS

European Search Report dated Jan. 1, 2002.

* cited by examiner

*Primary Examiner*—Max F. Hindenburg
*Assistant Examiner*—Brian Scott Szmal
(74) *Attorney, Agent, or Firm*—McDermott, Will & Emery

(57) ABSTRACT

Disclosed is a female physical condition managing apparatus comprising: a bioelectrical impedance-meter for determining BI values; a memory for storing the so determined BI values; a decision-making unit for making a decision about the monthly physical condition of a woman on the basis of the time series analysis of the variation of the BI values; and a display showing the so made decision on the monthly physical condition of the woman and a BI transition symbolic curve. This permits women to realize quickly what stage has been reached in the monthly physical condition. Presentation of measurement in the display is so dynamic that the viewer may not feel bored while the measurement is being made.

13 Claims, 44 Drawing Sheets

FIG. 2  woman A : variations of body temperature and values of BI between both feet (not modified with weight)

woman A : relation between weight and BI
(not modified with weight)

R: correlation coefficient representing the degree to which
two variables correlate.
Its value ranges from 0.0 to 1.0. As its value is getting
close to 1.0, two variables x and y converge toward
one and same (x=y for R=1). No correlation is found
for R=0.

woman A : relation between basal body temperature and weight-modified BI appearing between both feet R=correlation coefficient

FIG. 28

```
July 24, 2000  08:30
Today PMS!
  Swell level     ◊◊◊◊◊◊◊◊◊◊
  Feeling         ♥♥♡♡♡♡♡♡♡♡
  Body condition  ♥♥♥♥♡♡♡♡♡♡
  Skin condition  ♥♥♥♡♡♡♡♡♡♡
  Pheromone       ♥♥♡♡♡♡♡♡♡♡
```

FIG. 29

```
July 24, 2000  08:30
Today PMS!
  Attention to elephant foot-like
  deformation.
  Vitamin and Kalium required.
  Cooked pumpkin recommendable.
  Drink mineral-rich water.
```

Pregnancy possibility suggested.
   Better take pregnancy test.
```

| 28 day's cycle for averaging average weight 50Kg | ▲ ▼ |
|---|---|
| ■6/24～7/21···28 days' cycle    50Kg | |
| ■5/27～6/23···28 days' cycle    51Kg | |
| ■4/29～5/26···28 days' cycle    50Kg | |
| ■4/1 ～4/28···28 days' cycle    49Kg | |

July 24, 2000
Probably tomorrow PMS!

Attention to elephant foot-like deformation.
Vitamin and Kalium required.
Cooked pumpkin recommendable.
Drink mineral-rich water.

FIG. 37

```
July, 24 (Monday)

any intimate      ......  ↑YES   ↓NO
 contact ?

abnormal          ......  ↑YES   ↓NO
 bleeding ?

menstruation      ......  ↑YES   ↓NO
 period started ?
```

FIG. 38

```
July, 24 (Monday)

no intimate contact abnormal bleeding menstruation period started all correct ?            ↑YES   ↓ NO
```

| ← | | July, 2000 | | | | → |
|---|---|---|---|---|---|---|
| SUN. | MON. | TUES. | WED. | THURS. | FRI. | SAT. |
| | | | | | | 1 |
| 2 | 3 | 4 | 5 | 6 | 7 | 8 |
| 9 | 10 | 11 | 12 | 13 | 14 | 15 |
| 16 | 17 | 18 | 19 | 20 | 21 | 22 |
| 23 | 24 | 25 | 26 | 27 | 28 | 29 |
| 30 | 31 | | | | | |

FIG. 52

```
DEC. 30 (FRI.) 2000, 10:00 A.M.  ♪ ⊕ ▱

12. SUN.  MON.  TUES.  WED.  THURS.  FRI.  SAT.
                                       1     2
      3    4     5      6     7       8     9
     10   11    12     13    14      15    16
     17   18    19     20    21      22    23
     24   25    26     27    28      29   [30]
     31
```

FIG. 59

July. 30 (SUN) 2000, 10:00 P.M.

( PMS Preventing )  degree of swell:2

PMS Coming Soon

July. 30 (SUN) 2000, 10:00 P.M.

( PMS Preventing )  degree of swell:2

🯂 :Stretch

🯃 :Pumpkin

FEMALE PHYSICAL CONDITION MANAGING APPARATUS

BACKGROUND OF THE INVENTION

1. Field of the Invention

The present invention relates to a female physical condition managing apparatus which is capable of making a decision about the female physical condition which appears periodically in a female, for example, on the ovulation day, at the time of appearance of the premenstrual syndrome (hereinafter abbreviated as "PMS") for menstruation period or for the pregnancy-possible period.

2. Prior Art

The women's periodic body condition is related closely with their body temperature. The body temperature transfers from the low-temperature period to the high-temperature period on the ovulation day, and from the high-temperature period to the low-temperature period on the menstruation starting day, as shown in FIG. 1. Women take their body temperature every morning in bed to make manually a graphic record or table showing how the body temperature varies each and every day, thereby making it possible to determine which stage has been reached in the periodic physical condition.

It is necessary that women take their body temperature while laying themselves in bed, and it takes them about five minutes to measure their body temperature with body thermometers. This, however, is difficult to continue for a long time, and women often fall in sleep while taking their body temperature in bed.

A reliable decision can be made about some particular types of female physical condition on the basis of the body temperature, such as determination of the ovulation day, the menstruation period and the pregnancy-possible period, all of which are useful factors for birth control. Determination about whether women undergo the PMS has been increasingly in concern from the point of women's daily life, but such decision is impossible with recourse to the recording of body temperature. The PMS starts seven days earlier than the beginning of the menstruation period, causing women to suffer from headache, irritation, stomachache, swell or any other unpleasing symptom. When they realize that their unpleasing symptoms are caused simply by the PMS, they can be released from their sufferings significantly.

As a matter of fact determination of female physical condition from the graphic record of body temperature is difficult, and such determination is apt to be dependent on her discretion.

As is the case with a conventional percent fat measurement-and-weight scale, it takes a significant length of time to measure a required quantity, and the user is apt to feel bored while making the required measurement. In the hope of reducing such boredom the result of the measurement is given in the form of a train of same figures extending with time. Presentation of same figures, however, causes motionless effect to viewers. Some people, therefore, still feel bored.

SUMMARY OF THE INVENTION

One object of the present invention is to provide a female physical condition managing apparatus which provides a quick decision on the periodic physical condition including the PMS.

Another object of the present invention is to provide such a female physical condition managing apparatus permitting users to be released from feeling bored while making a required measurement or decision-making.

To attain this object a female physical condition managing apparatus according to the present invention comprises: a bioelectrical impedance meter for determining values of bioelectrical impedance or BI values; a memory for storing the so determined BI values; a decision-making unit for making a decision about the monthly physical condition of a woman on the basis of the time series analysis of the variation of the BI values; and a display for showing the so made decision on the monthly physical condition of the woman and a BI transition symbolic curve. Hereinafter, the word, "bioelectrical impedance" is abbreviated as "BI".

The period of BI transition symbolic curve may span from the menstruation to the next menstruation.

The monthly physical condition may include at least the delicate period, dieting period, pre- and post-ovulation, PMS preventing period, PMS period or post-delicate period.

The display may show at least one of the degree of swell, the date of the physical condition decided and the weight measured at the time the required measurement was determined.

The display may have a given mark moving on a BI transition symbolic curve while the required measurement is being effected or while the required decision is being made.

The display may show, in synchronism with the movement of the mark, the name identifying the period of physical condition and/or a swell-symbolic shape illustrating the degree of swell.

The display may have a given mark moving on a monthly periodic chart while the required measurement is being effected or while the required decision is being made.

The monthly periodic chart may be a sinusoidal curve, a circle or a straight line.

The mark may be a circle o or an animal figure.

The mark may vary every month and/or every day in shape and/or color.

The display may be capable of retrieving selected data of measurement from an associated memory and of showing such data by means of telop while the required measurement is being effected or while the required decision is being made.

The display may give an animation-like presentation of monthly period while the required measurement is being effected or while the required decision is being made.

The animation-like presentation of monthly period may be composed of a series of figures illustrating how a chick appears from an egg.

The animation-like presentation of monthly period may be composed of a series of figures illustrating how the moon varies from crescent to full moon.

Other objects and advantages of the present invention will be understood from the following description of some preferred embodiments of the present invention.

BRIEF DESCRIPTION OF DRAWINGS

FIG. 28 illustrates how the cyclic messages are given in the display;

FIG. 29 shows the advice messages appearing in the display;

FIG. 30 shows a message informing the user of pregnancy possibility in the display;

FIG. 31 illustrates how the measurement results of weight and percent fat are shown in the display;

FIG. 32 shows the 28 days' cycle measurements of weight and percent fat;

FIG. 37 shows some items to be selected in logging a diary;

FIG. 38 shows the selected items for confirmation;

FIG. 52 shows a calendar image of the present month appearing initially in the display;

FIG. 59 illustrates an image showing an advisory message in the display;

FIG. 60 illustrates an image showing the advisory message pertaining to foods and exercise;

DESCRIPTION OF PREFERRED EMBODIMENTS

Before entering the description of a female physical condition managing apparatus according to the present invention the relation between the BI and the women's periodic physical condition is described by referring to the data of actual measurement. Women took their body temperatures every morning when getting up, and the values of BI were measured between both feet.

Figure 1:
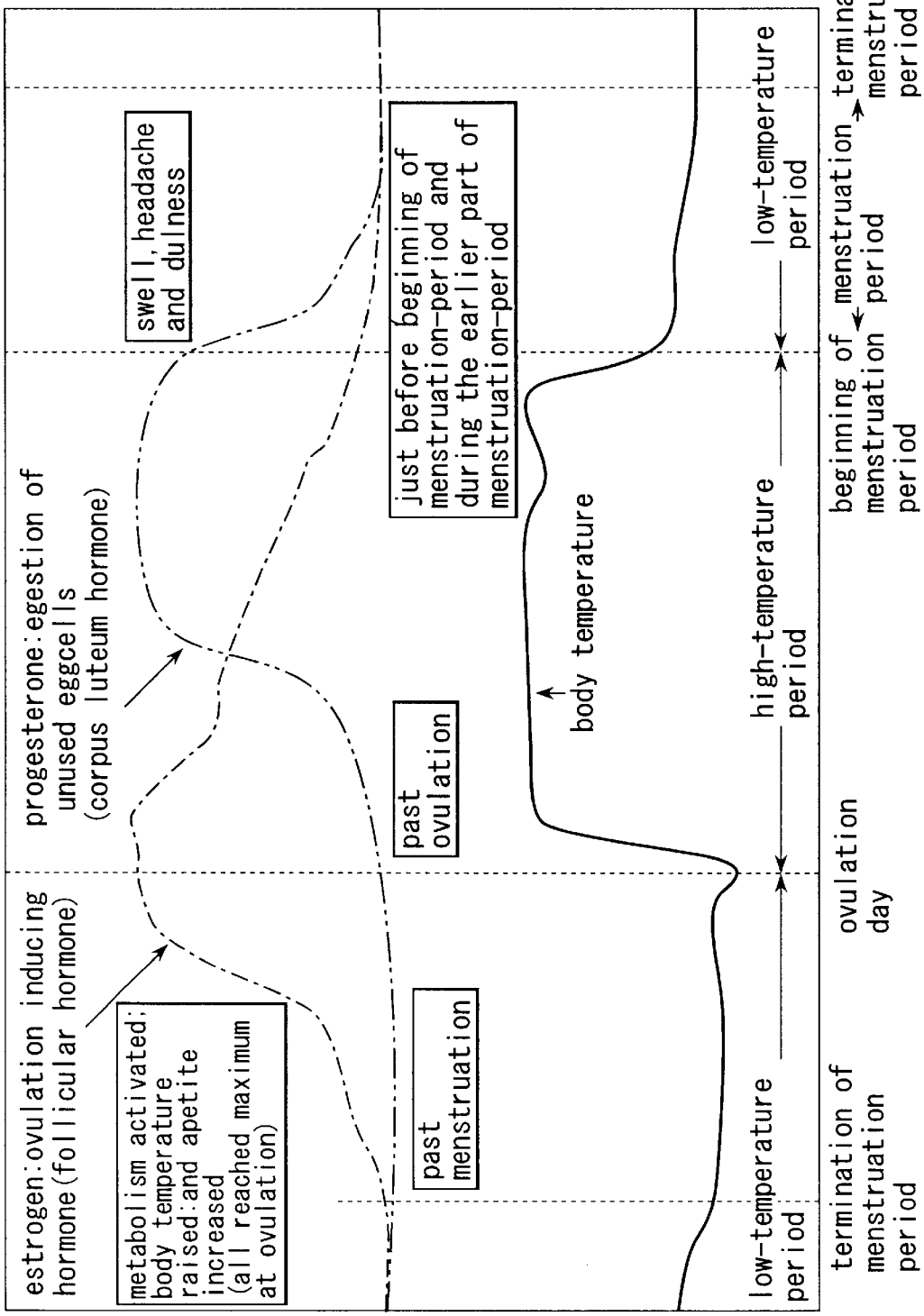
FIG. 1 shows how the monthly periodic physical condition of women, the body temperature and the secretion of hormone are related with each other.
Figure 2:
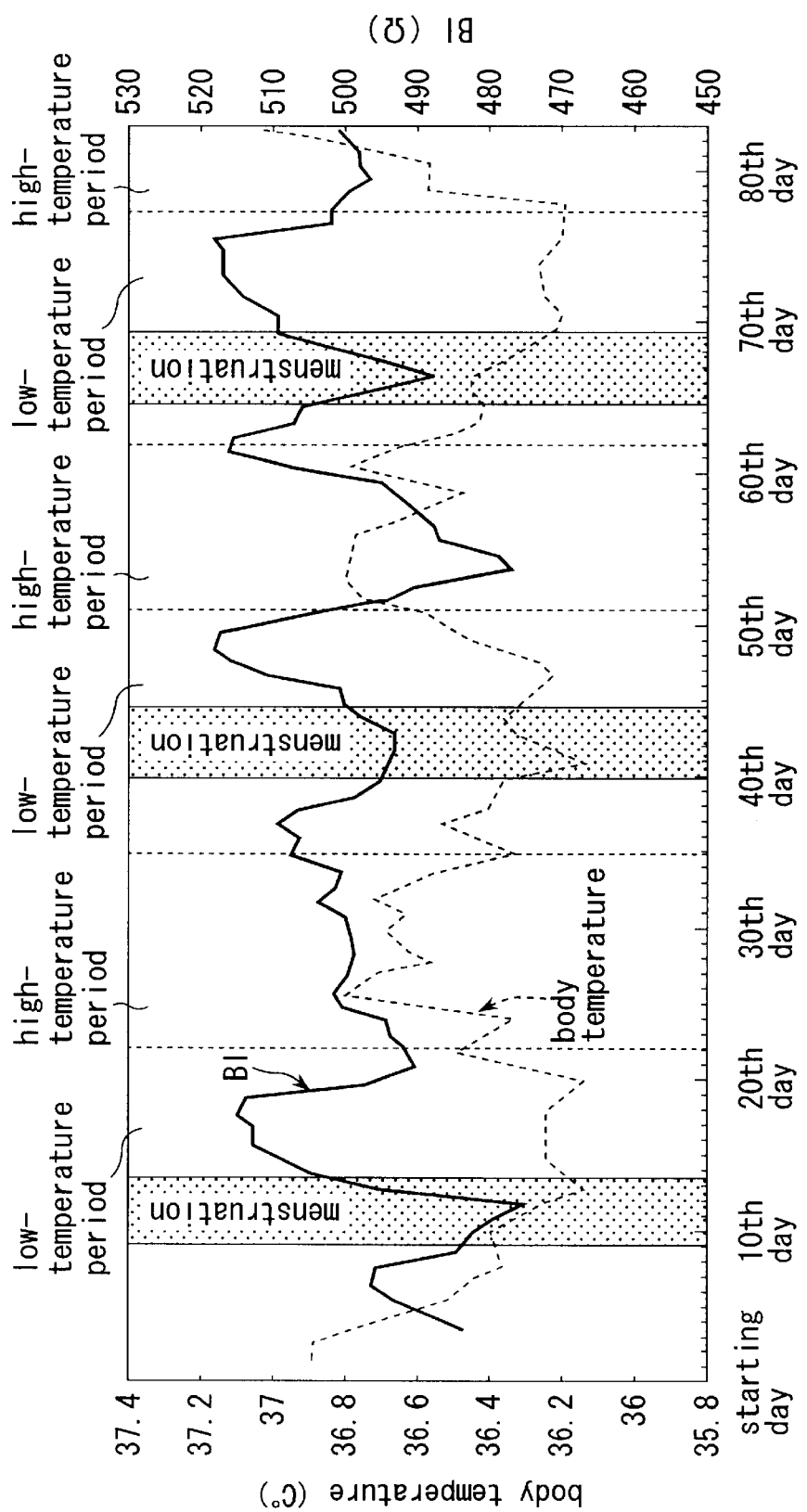
FIG. 2 illustrates how the body temperature and BI vary with day.

First, described is the periodic BI variation. FIG. 2 shows how the body temperature and BI of a selected woman A vary with day. The graphs were made by plotting the average values of two adjacent ones, which average values were determined according to the method of moving average. As a general tendency the values of BI remain high while the body temperature remains low. The values of BI remain low while the body temperature remains high, and the BI curve descends in the early half of the menstruation period after rising before the beginning of the menstruation period.

Figure 3:
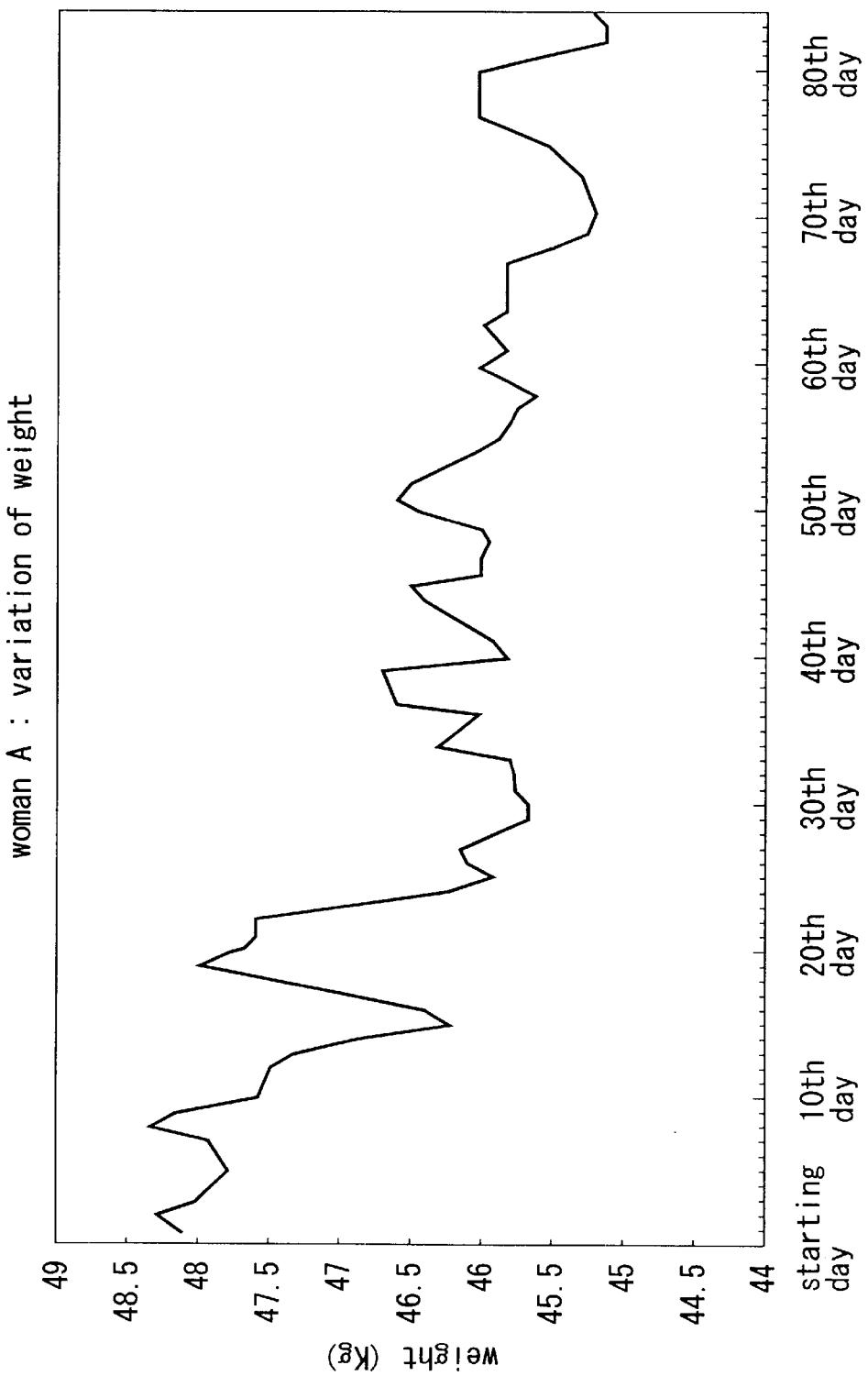
FIG. 3 illustrates how the weight varies with day.
Figure 4:
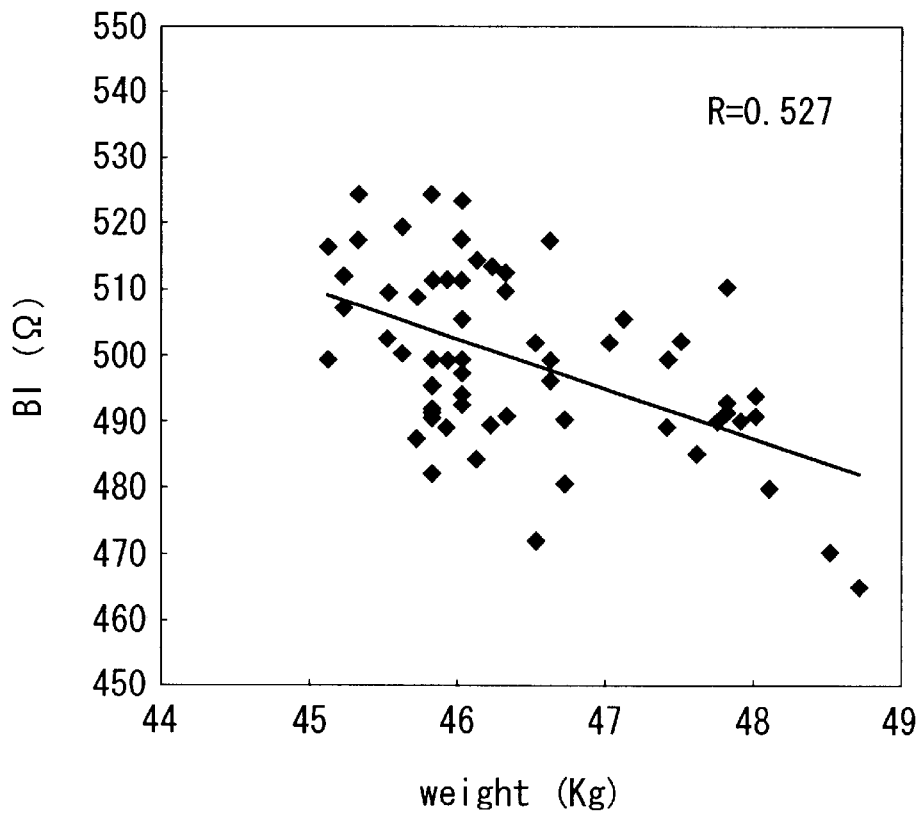
FIG. 4 illustrates how the weight and BI are correlated.

Next, the relation between the values of BI and the weight is described. FIG. 3 shows how the weight of the woman A varies while her physical condition was being monitored. The weight decrease gradually during measurement. FIG. 4 shows how the weight is correlated with the values of BI. A significant negative correlation between the weight and the values of BI was found (correlation coefficient R=0.527). As shown, the weight decreases with the increasee of the values of BI, and vice versa. This inclination appears to be attributable to the fact that: the water content of the female body increases (decreases) with the increase (decrease) of the weight; and the value of BI decreases (increases) with the increase (decrease) of the water content. It appears that the BI curve of FIG. 2 be affected by the decreasing weight of the woman A as shown in FIG. 3 and that the BI curve need be corrected by modifying the values of BI with weight.

Figure 5:
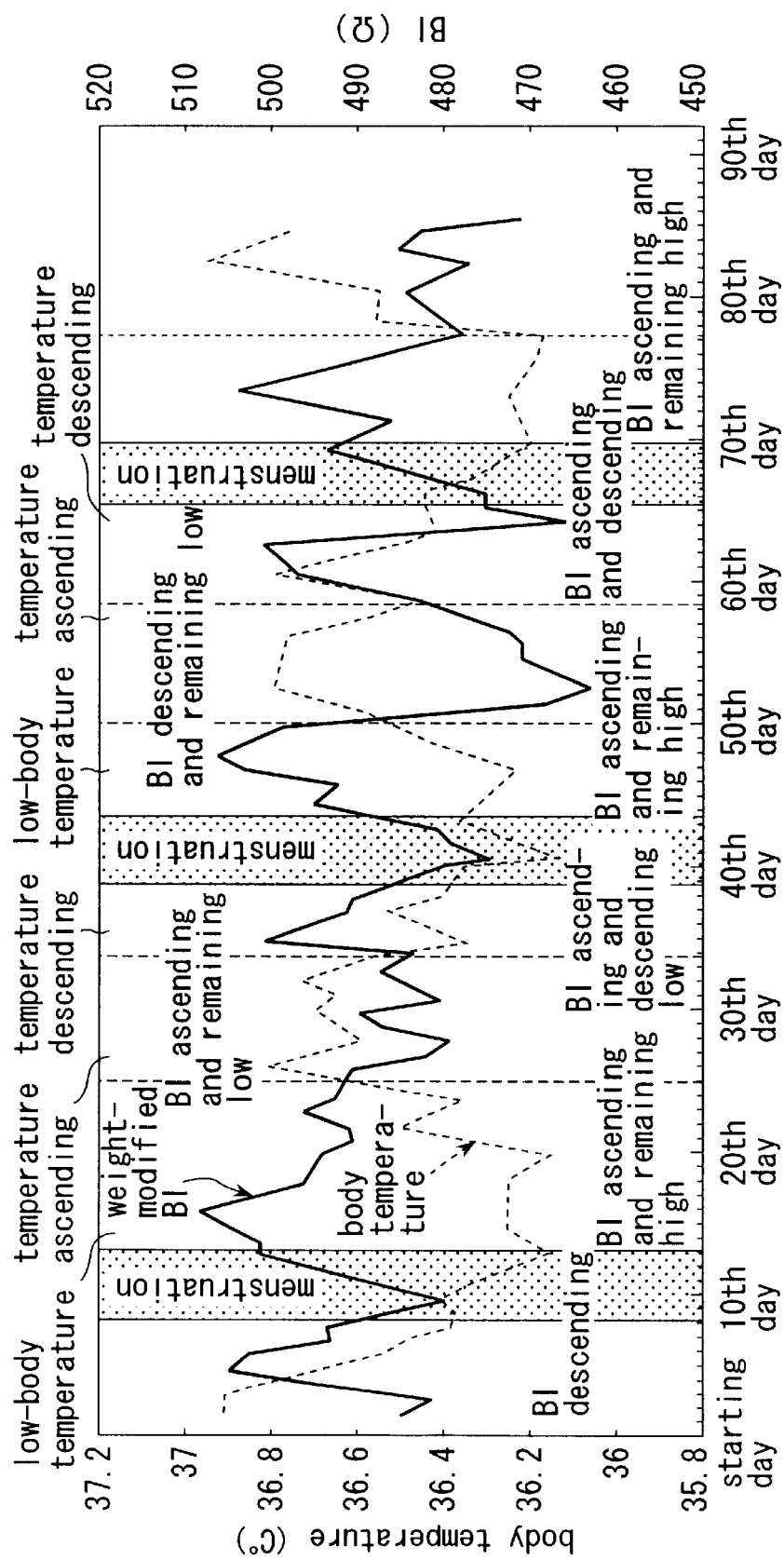
FIG. 5 illustrates how the weight-modified BI varies with day.

FIG. 5 shows the weight-modified BI curve, so that it may be made independent from the weight variation. Specifically the BI curve of FIG. 2 is modified according to Equation of Correction 1 or 2:

$BI$ modified with weight=$BI$+$A$×(difference of weight from the initial weight)     (1), or $BI$ modified with weight=$BI$+$B$×(difference of weight from the preceding weight)     (2), where "A" and "B" stand for correction coefficients.

The weight-modified BI curve of FIG. 5 shows the periodic variation of BI more clearly than the BI curve of FIG. 2, which is affected more or less by the variation of the weight.

Figure 6:
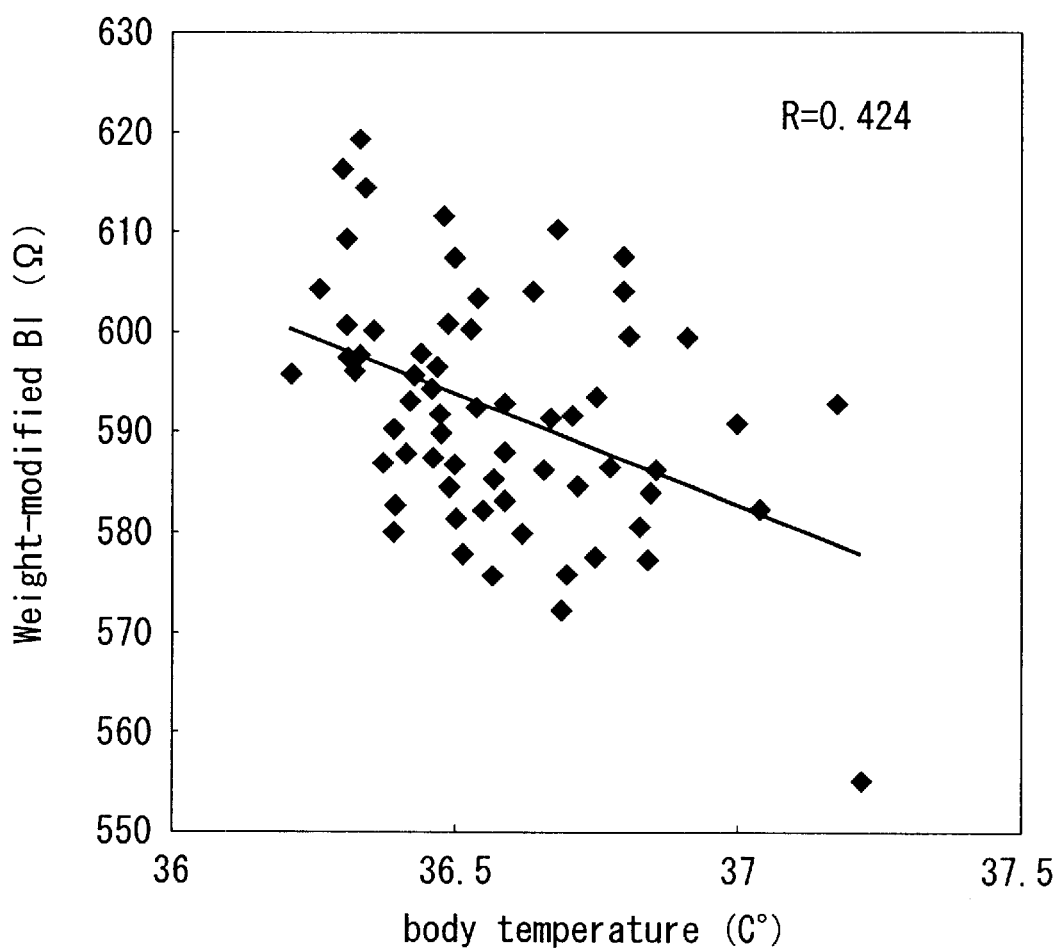
FIG. 6 illustrates how the weight-modified BI and the body temperature are correlated.

Next, the BI-to-body temperature relationship and the BI-to-PMS relationship are described. As seen from FIGS. 2 and 5, the values of BI decrease for a specific period spanning from the proximity to the menstruation beginning to the end of the early half of the menstruation period, for which specific period the body temperature decreases, too. Except for the specific period the values of BI remain high while the body temperature remains low. Because of this inconsistency there is little significant correlation between the body temperature and the values of weight-modified BI (correlation coefficient R=0.424) as shown in FIG. 6.

The decending of BI curve for the specific period (the body temperature descending) appears to be attributable to the swell of women's bodies; the water content of women's body is so high that the BI value may decrease significantly. Thus viewed, the values of BI and the swell are related as follows: as the swell appears, the values of BI decrease, and as the swell disappears, the values of BI increase. This suggests that a decision as to whether the swell appears in women's bodies can be made in terms of the values of BI. Apparently such a decision is impossible on the basis of the variation of body temperature. It is well known that appearance of the swell prior to the menstruation period is closely related with the PMS. Specifically the PMS accompanies the swell in women's bodies, and the PMS is liable to get worse as the swell increases in size. This suggests that a decision as to whether the woman undergoes the PMS can be made on the basis of the variation of BI, as is the case with the swell.

Figure 7:
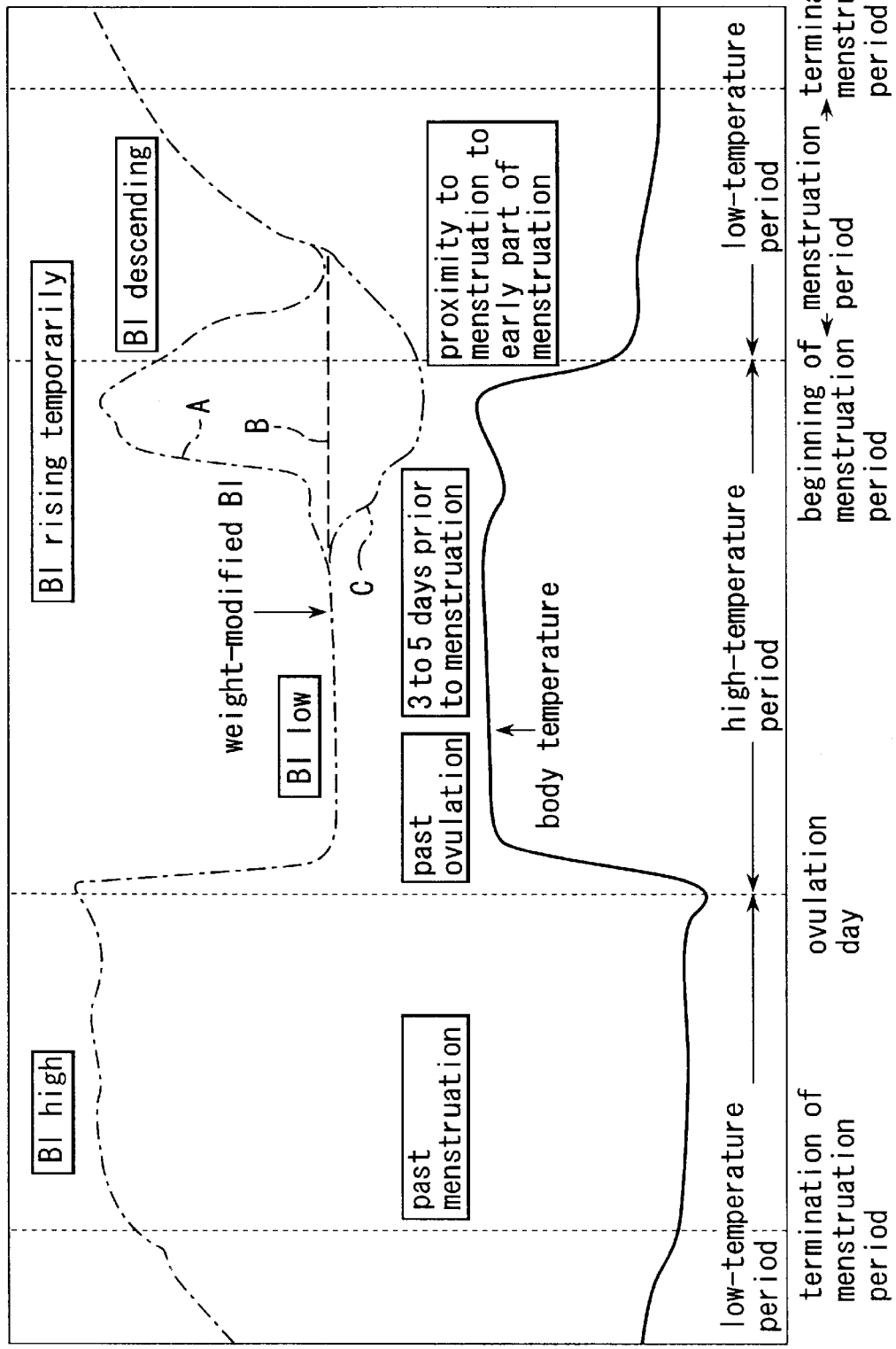
FIG. 7 illustrates how the weight-modified BI, the monthly periodic physical condition and the body temperature are related.
Figure 8:
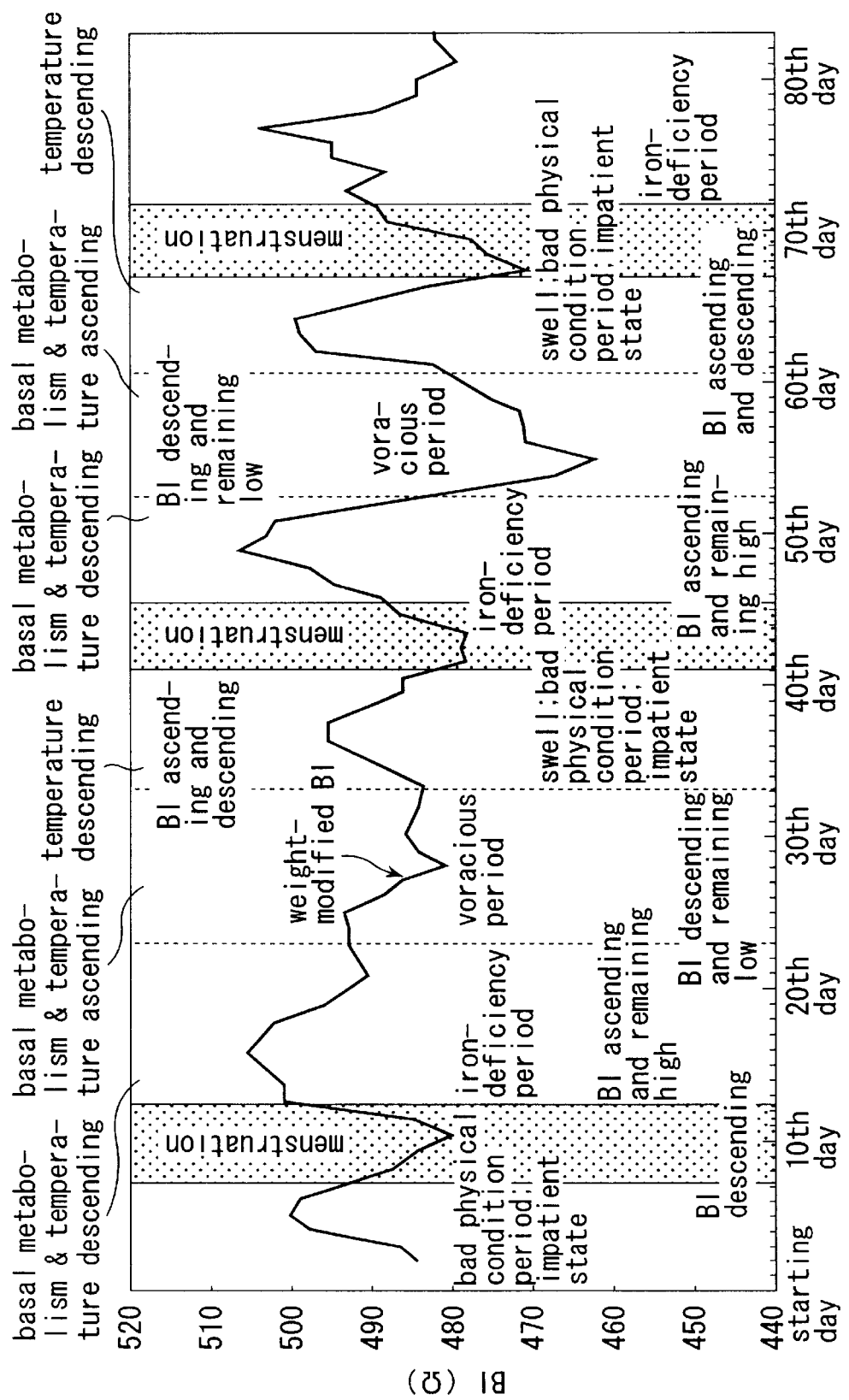
FIG. 8 illustrates how the weight-modified BI, the monthly periodic physical condition and the body temperature are related.

FIGS. 7 and 8 illustrate how the weight-modified values of BI and the body temperature are related with the monthly variation of female physical condition. These graphs show clearly that the BI curve is closely related with the monthly variation of female physical condition. This suggests that a decision on the monthly variation of female physical condition can be made on the basis of the BI curve, as for instance, follows: the ovulation day can be expected from the high-to-low transition of BI curve. Likewise, appearance of the swell or the PMS can be expected. Termination of the PMS can be decided from the rise of the BI curve. Also, termination of the menstruation period can be decided from the BI curve remaining stable at high level. There appear three different phases noticeable from the BI curve in the PMS-prevailing period. As seen from FIG. 7, the BI curve rises and falls just before the beginning of the menstruation period (noticeable from women of Type A). From the rise-and-fall of the BI curve it may be expected that this type of women undergo the PMS. The BI curve remains constant for women of Type B whereas the BI curve decreases for women of Type C. The descendent of the BI curve accompanies an irritation characteristic of PMS and appearance of the swell.

The values of BI were determined by measuring bioelectrical impedance appearing between woman's feet. The same results as described above were confirmed on so numerous women that the proposed method may be justly applied to diagnosis of women's periodical physical and mental condition. Measurement of bioelectrical impedance between both hands or one hand and one foot may be permitted, but measurement of bioelectrical impedance between both feet is most appropriate for the purpose because of the symptoms being clearly discernible from the BI curve provided by such inter-feet measurements.

Now, some embodiments of the present invention are described below with reference to drawings.

Figure 9:
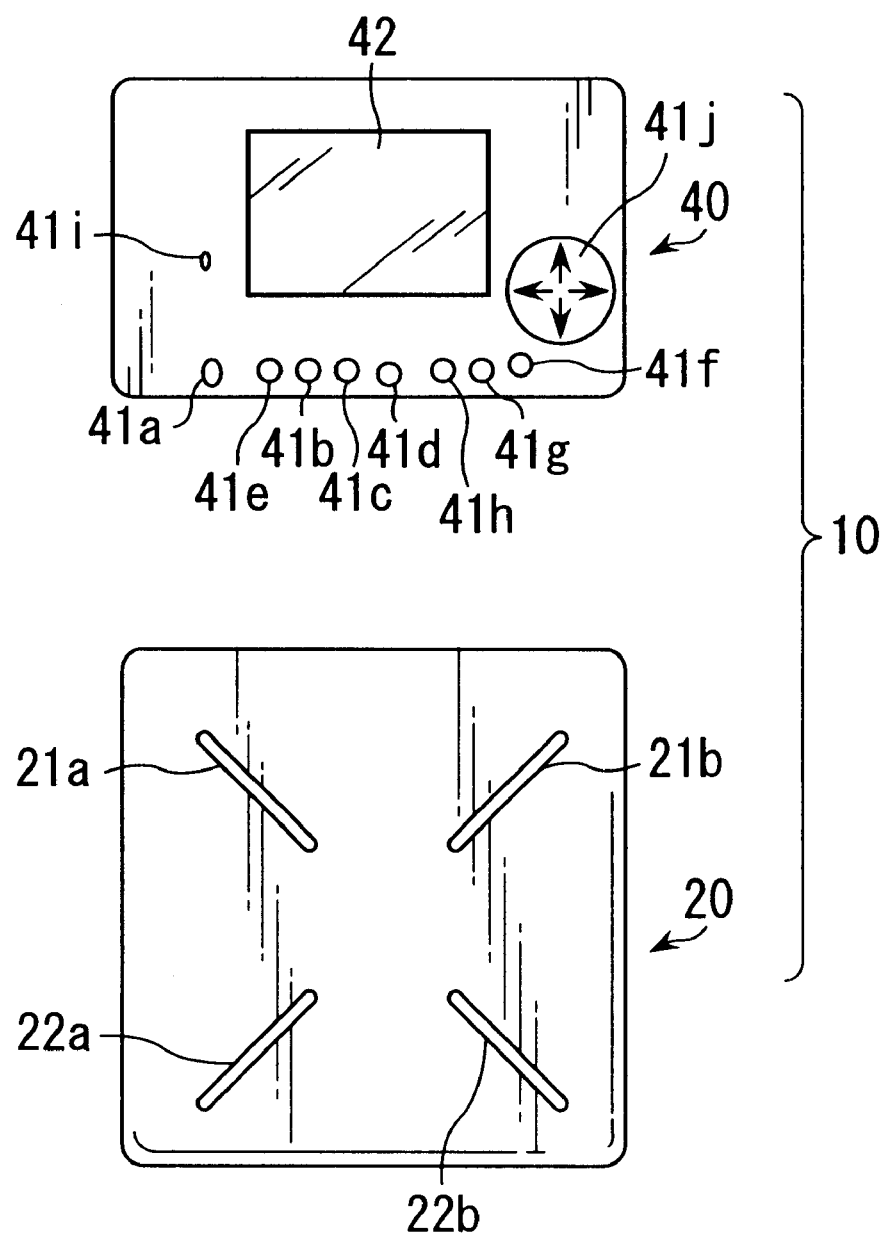
FIG. 9 illustrates how a female physical condition managing apparatus according to a first embodiment looks in appearance.

FIG. 9 shows the appearance of a female physical condition managing apparatus 10 according to a first embodiment. It comprises a scale-and-bioelectrical impedance meter 20 and a control box 40 connected to the scale-and-bioelectrical impedance via infrared or radio wave or via an electric cable. The scale-and-bioelectrical impedance meter 20 has constant current feeding electrodes 21a and 21b and voltage measuring electrodes 22a and 22b provided on its front side whereas the control box 40 has a group of operation buttons 41a to 41j and a display 42 provided on its front side. The group of operation buttons include a power source button 41a, a measurement button 41b, a registration button 41c, a transmission button 41d, a menstruation button 41e, a decision button 41f, a mode selection button 41g, a cancel button 41h, a reset button 41i and a direction button 41j. The direction button 41j has four button sector bearing directional indications →, ←, ↑ and ↓ thereon.

Figure 10:
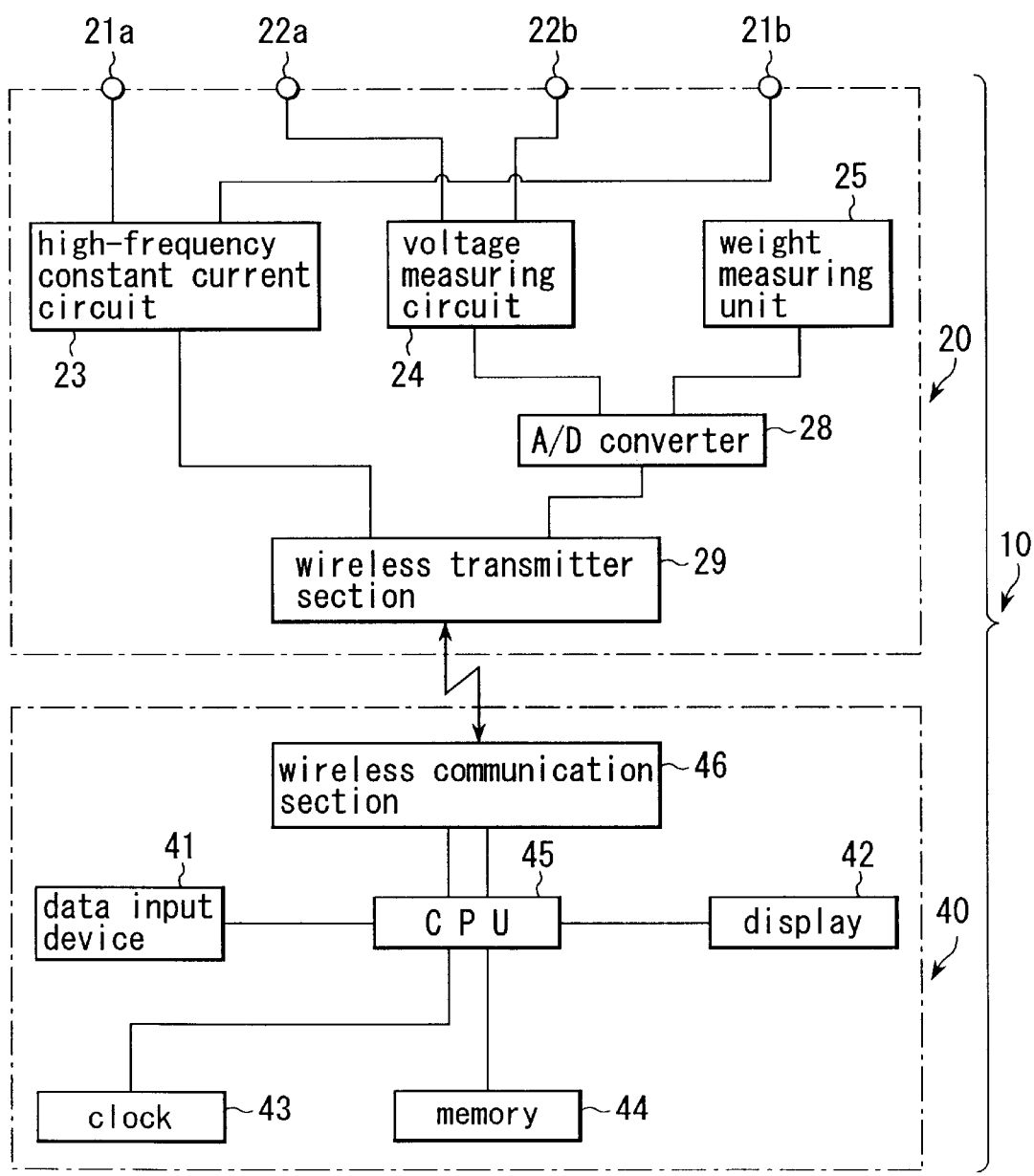
FIG. 10 is a block diagram showing the functions of the female physical condition managing apparatus.

FIG. 10 is a block diagram showing the functional structure of the female physical condition managing apparatus 10. The scale-and-bioelectrical impedance meter 20 comprises a high-frequency constant current circuit 23 for supplying a weak high-frequency constant current of fixed value to the constant current feeding electrodes 21a and 21b, a voltage measuring circuit 24 for measuring the voltage appearing between the voltage measuring electrodes 22a and 22b, a weight measuring unit 25, an A/D converter 28 for converting the measured voltage and weight to digital values and a wireless transmitter section 29.

In addition to the data-inputting buttons 41a to 41j and the display 42 for displaying the variation of BI, the determined physical condition and such like, the control box 40 comprises a clock 43 for showing on what day and time the measurement is effected, a memory 44 for storing the measured values of BI, the day and time at which measurements are effected, a CPU 45 for making a decision on the female physical condition on the basis of data pertaining to the menstruation period inputted by the data input device 41 and the measured values of BI, and a wireless communication section 46.

In this particular embodiment the scale-and-bioelectrical impedance meter 20 and the control box 40 make up the female physical condition managing apparatus. The scale-and-bioelectrical impedance meter 20 and the control box 40 may be combined as a whole.

Now, the manner in which the female physical condition managing apparatus works is described.

Figure 12:
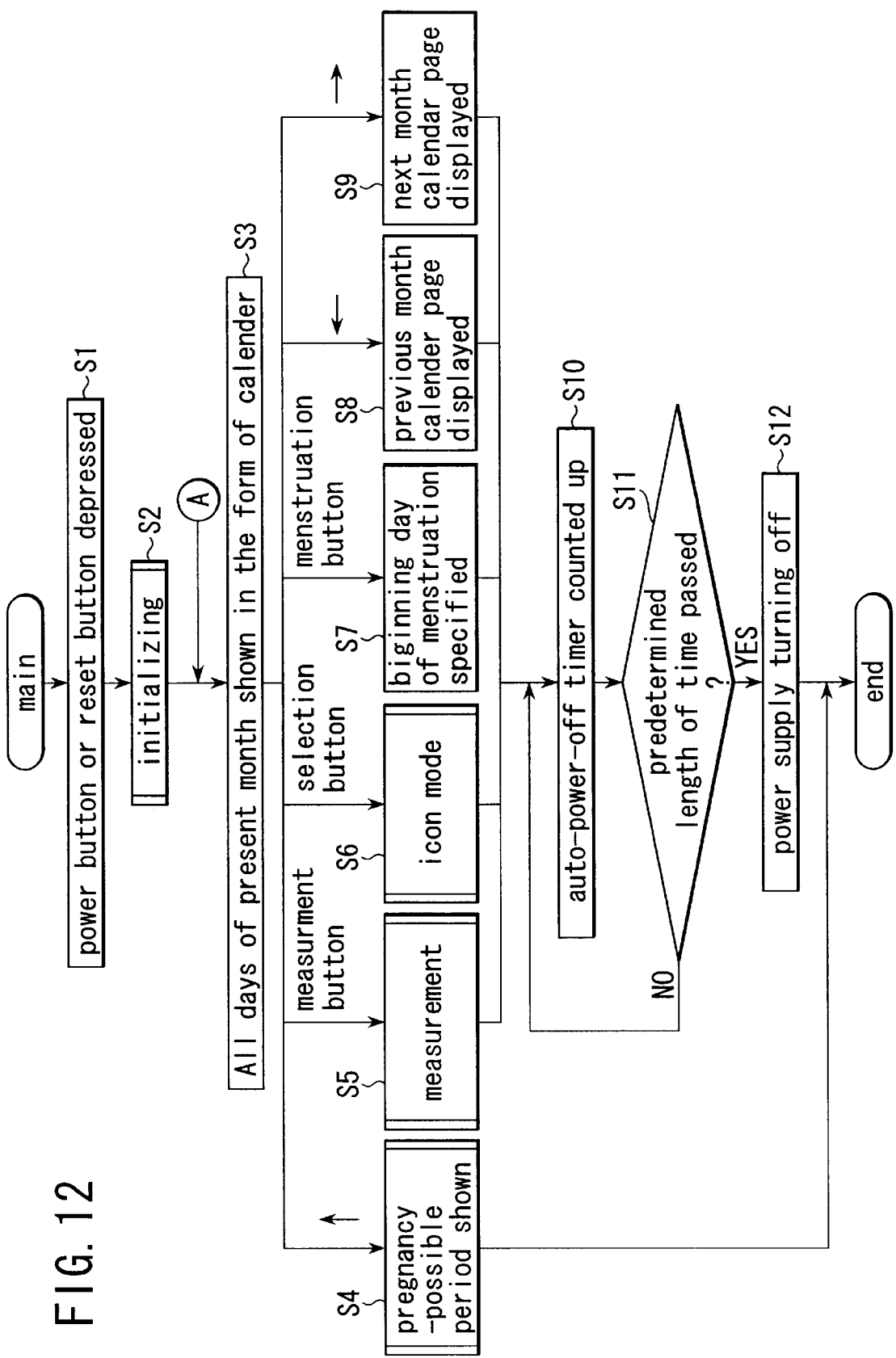
FIG. 12 is a flow chart showing the proceeding by which a decision is made on the monthly periodical physical condition.

FIGS. 12 to 18, 20 and 21 show the flowcharts describing the operation of the apparatus. FIG. 19 shows how selected phases of operation are shifted to each other by depressing selected operation buttons. First, referring to FIG. 12 showing the main program, the power button 41a is depressed at STEP S1, thereby putting the apparatus in circuit with the power supply. The apparatus is initialized at STEP S2 as later described in detail. All the days of the present month are shown in the form of calendar in the display 42 at STEP S3, as seen from FIG. 22. Different icons for commands appear on the heading of the screen. The figure 24 encircled with a rectangle represents the present day.

By depressing the button sector ↑ of .the direction button 41j, the measurement button 41b, the selection button 41g, the menstruation button 41e or the button sector ← or → of .the direction button 41j, S4, S5, S6, S7, S8 or S9 is executed, respectively.

At STEP S4 the apparatus works in the pregnancy-possible period presenting mode, thus displaying days corresponding to the expected start of the menstruation period and the possibility of pregnancy in the form of calendar. At STEP S5 the apparatus works in the measurement mode in which: the value of bioelectrical impedance and other factors are determined; and the results of the measurements are displayed. Some details are described later. At STEP S6 the apparatus works in the icon mode, in which any command selected by marking which one of the icons appearing in the calendar page may be executed. Some details are described later.

At STEP S7 the day of menstruation is specified on the calendar page. At STEP S8 the calendar page of the previous month appears on the screen. At STEP S9 the calendar page of the next month appears on the screen. At STEP S10 the auto-power-off timer is counted up. The timer permits disconnection from the power supply after the predetermined length of time has passed, and is reset in response to the turning-on of the power supply or to key depression. At STEP S11 a decision is made as to whether the predetermined length of time has passed. In the negative case the proceeding returns to STEP 10. At STEP S12 the power supply is made to turn off.

Figure 13:
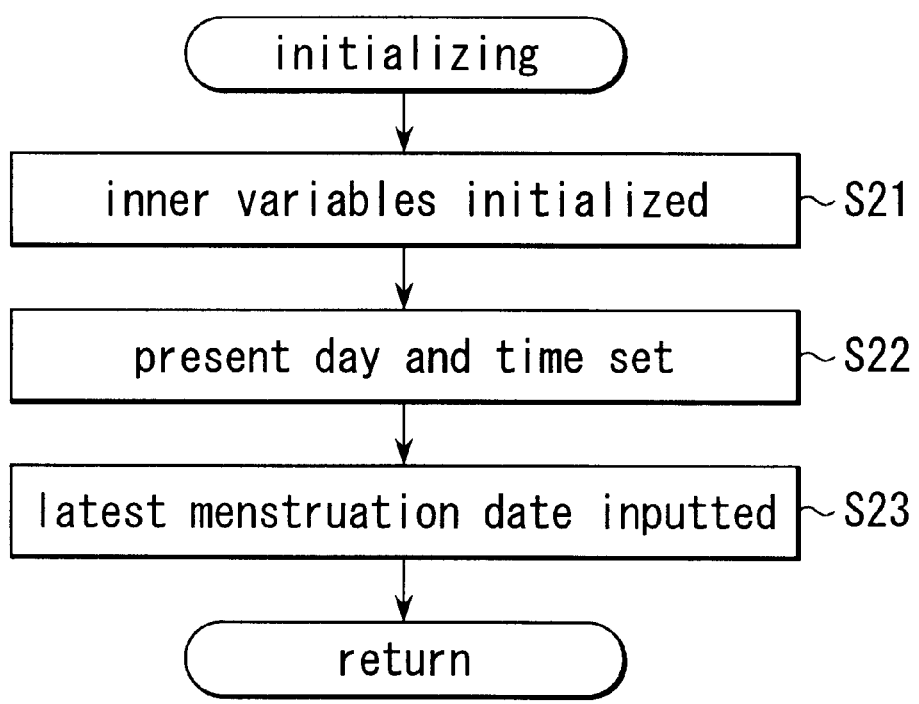
FIG. 13 is a flowchart according to which the initialization is performed.

Referring to FIG. 13, the initializing process (STEP S2) can start only when the power supply button is depressed for the first time or when the resetting button is depressed. A decision can be made as to whether the power supply has turned on before (in the affirmative case no initialization required); an initializing flag is set when the initialization has been completed, and therefore, at the first step it is necessary to check whether the flag has been set, and in the affirmative case no initialization is required.

At STEP S21 all inner variables are initialized. At STEP S22 the clock 43 is set for the present day and time. At STEP S23 the beginning day of the latest menstruation period or latest menstruation date is inputted.

Figure 14:
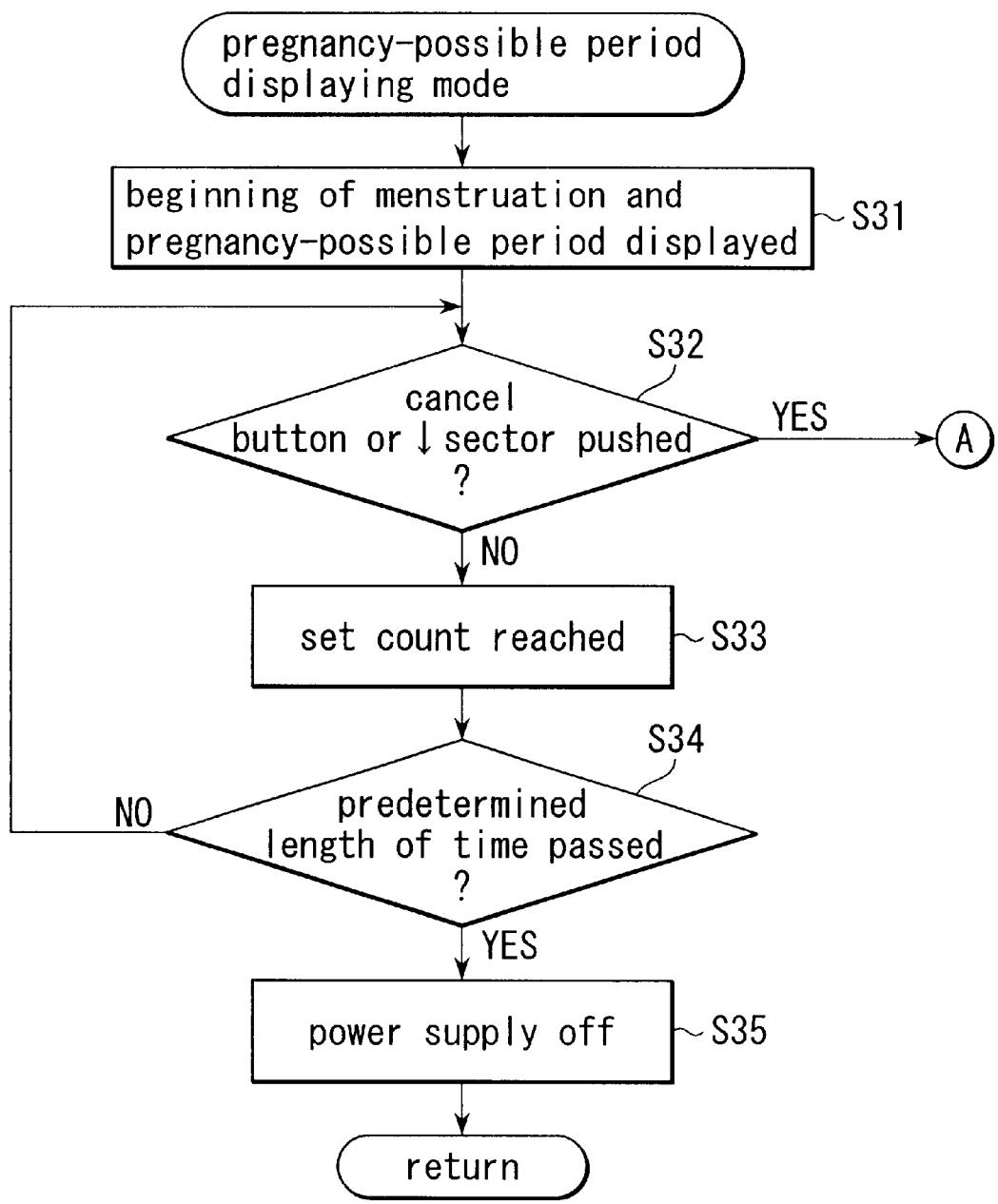
FIG. 14 is a flowchart showing the pregnancy-possible period presenting mode.

Referring to FIG. 14, the pregnancy-possible period displaying mode (STEP S4) is described below. No corresponding icon appears in the screen because the relevant information needs to be kept confidential. At STEP S31 the pregnancy-possible period and the beginning day of the menstruation period (or beginning of menstruation) are shown on the screen, as seen from FIGS. 23 and 24. Specifically in FIG. 23 the ovulation day is indicated by a double circle ◎, and the words, "GOOD" sandwiching the double circle ◎ represent the pregnancy-possible period. The double-circle and the words appear alternately with the days hidden behind, blinking all the time. The figure 24 encircled with a rectangle represents the present day.

Figures 22, 23, 24:
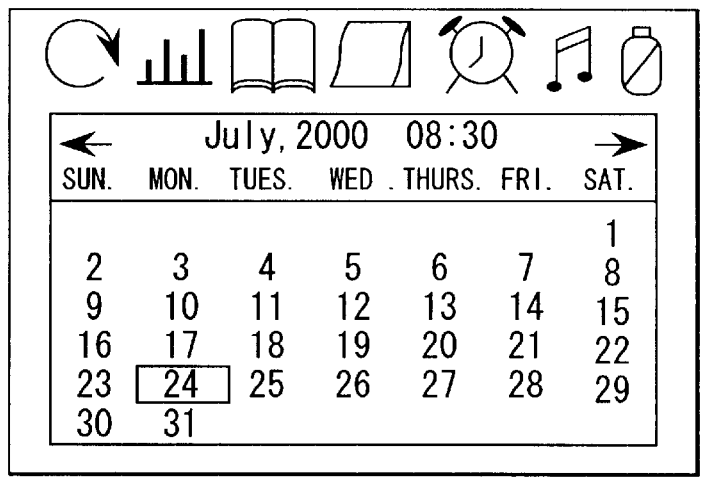
FIG. 22 is the initial image appearing in the display.
FIG. 23 illustrates how the pregnancy-possible day is indicated on a given page of the calendar.
FIG. 24 illustrates how the expected beginning day of the menstruation period is indicated on a given page of the calendar.

Referring to FIG. 24, the expected menstruation beginning day is indicated by the letter M, and the letter and the expected day appear alternately, and blink. In a case where the pregnancy-possible period and the menstruation beginning day span two months, the arrow icon → blinks at the upper, right corner (see FIG. 23). The arrow button sector is depressed so that the next month calendar page appears (see FIG. 24). The next month calendar page has an arrow icon blinking on its upper left corner. In this example the pregnancy-possible period is five days long, including two days before and after the ovulation day. In another example the pregnancy-possible period is determined to be nine days long, including the nineteenth to eleventh days counted backward from the day previous to the subsequent expected menstruation beginning day.

At STEP S32 a decision is made as to whether the cancel button 41h or ↓ button sector was pushed or not. In the affirmative the proceeding returns to the STEP S3, and then, the pregnancy-possible period presenting mode is finished. At STEP S33 the timer reaches the set count. At STEP S34 a decision is made as to whether the predetermined length of time has passed or not. In the negative the proceeding returns to STEP S32. In the affirmative the proceeding goes to STEP S35, where the power supply is disconnected.

Figure 15:
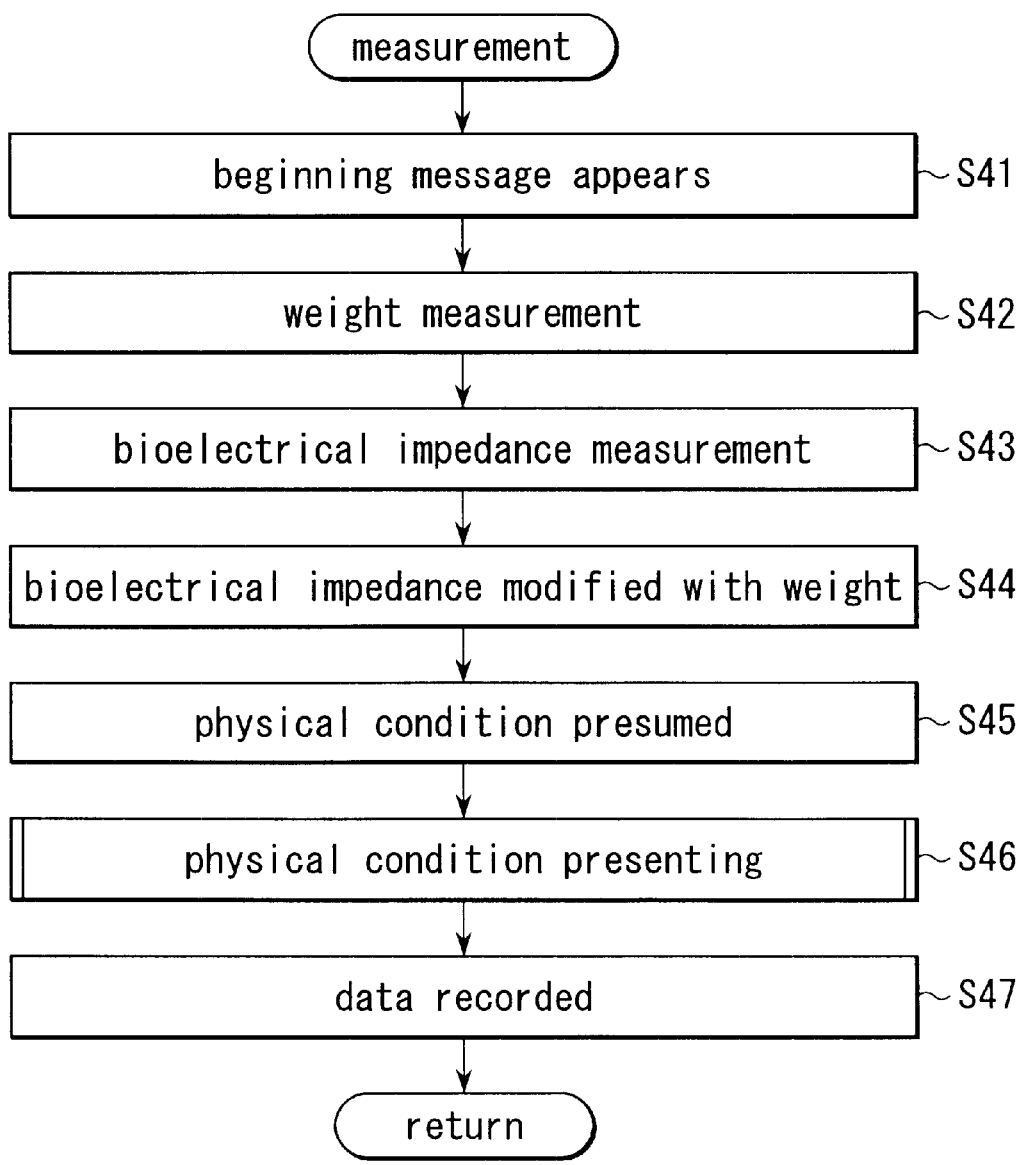
FIG. 15 is a flow chart according to which required measurements and estimations are made.
Figure 25:
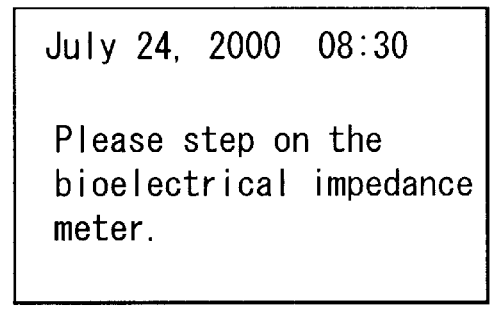
FIG. 25 shows one example of a message describing what the user is requested to do at the start of a required measurement.

Referring to FIG. 15, the measurement processing (STEP 5) is described in detail. At STEP S41 a message reading "Please step on the bioelectrical impedance meter." appears and blinks in the display, as seen from FIG. 25. At the same time the date and time appear at the heading of the screen. When the cancel button 41h is pushed, the proceeding returns to STEP S3.

At STEP S42 the user stands on the bioelectrical impedance meter 20 equipped with the weight scale. Specifically she stands on the bioelectrical impedance meter with the toes and heels of the left and light feet put on the constant current feeding electrodes 21a and 21b and the voltage measuring electrodes 22a and 22b respectively. Now, the measurement starts with the weight of the user. At STEP S43 a high-frequency, constant current circuit 23 makes a high-frequency, weak current flow in her body via the constant current feeding electrode 21a, the toe of the left foot, the left leg, the lower part of her abdomen, the right leg, the toe of the right foot and the constant current feeding electrode 21b. A voltage measuring circuit 24 determines the voltage appearing between the voltage measuring electrodes 22a and 22b, thus determining the value of BI. The CPU 45 allows the display to show a sinusoidal wave of monthly-period curve as seen from FIG. 26. A chick character and a white square move on the sinusoidal curve back and force. A linear or circular curve may be used in place of the sinusoidal curve. The chick character may be replaced by another lovely animal shape. Some measurement data may be retrieved from the memory 44 to be shown by means of television opaque projector. This has the effect of releasing from the boring condition while waiting for the result. The white square □ may be replaced by the circle ○ or ●. The chick character may be changed in color or shape each and every month or day. The value of BI determined at STEP S44 is modified according to the weight-modification equation (1) or (2) as described above to provide the weight-modified BI value.

At STEP S45 the present physical condition is determined in consideration of the female physical condition-and-bioelectrical impedance relationship. The required determination can be made on the basis of the present weight-modified BI (which is determined at STEP S44), the previous weight-modified BI (which is retrieved from the memory 24) and data collected for the menstruation period as follows:

the menstruation beginning day has been specified at STEP7 in FIG. 12, and is regarded as the beginning day of the menstruation period, and the week counted forward from the beginning day of the menstruation period is called "First Period" (menstruation period). The "Second Period" (Good Condition Period) spans from the day following the termination of the "First Period" to the day previous to the first day on which the BI value is measured to be 4% less than the average BI value of the Second Week of the previous monthly record. The "Third Period" (Steady Period) spans from the day following the termination of the "Second Period" to the day one week backward from the beginning day of next menstruation period, which beginning day is presumed to be from the history or past record of female physical condition. Finally, the "Fourth Period" (PMS period) spans from the day following the termination of the Third Period to the specified beginning day of the next menstruation period. Appearance of PMS can be determined by making a decision as to which type of graphic variation appears at the transition to the rise of BI curve, TYPE A, B or C (see FIG. 7). Specifically when the present physical condition is found to be of TYPE A, the appearance of PMS may be presumed. The ovulation day may be justly determined as falling on the fourteenth day counted backward from the beginning day of next menstruation period, which beginning day is determined from the past record of data. The ovulation day is the last day of the "Good Condition Period", and if the ovulation day should fall on the day following the last day, the pregnancy-possible day needs to be corrected accordingly.

The practice of a decision being made as described requires the past record of data, which was made at least one month previous to the decision making. In a case where no prior record is available, the message which reads "required data unavailable" appears in the display.

Now, the manner in which a decision is made as to whether the swell characteristic of PMS appears is described below. The average value of BI is determined from those recorded for a selected PMS period in the past, and the so determined average BI value is used as the STANDARD. Specifically the degree of swell is determined as SWELL LEVEL 1 when the BI value decreases 1% down with respect to the STANDARD, and the degree of swell rises one level high each time the BI value has decreased 1%

At STEP S46 the measurement and decision is completed to show the so decided physical condition in the display, as later described in detail. At STEP S47 the → button sector is depressed, or otherwise, the predetermined length of time has passed, and then, the message which reads "Push the record button to record the data." appears in the display. The record button 41c is pushed to store in the memory 44 the weight-modified BI value and the weight, both of which are determined this time. Then, the proceeding returns to the main program.

Figure 16:
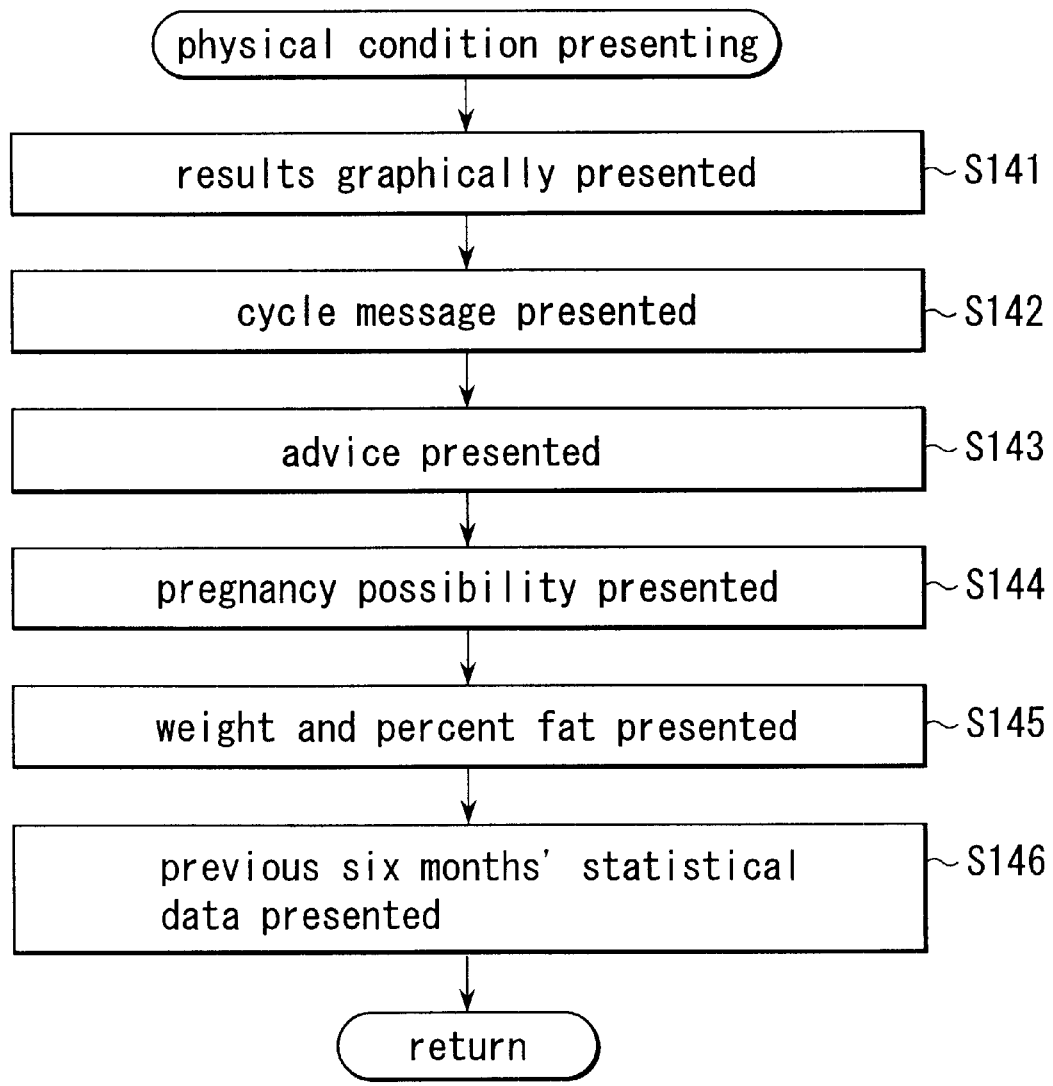
FIG. 16 is a flow chart showing a series of steps for displaying the physical condition.
Figure 27:
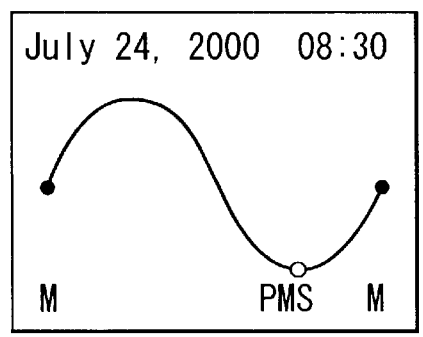
FIG. 27 illustrates how the display indicates a decision made on the physical condition.

Referring to FIG. 16, the physical condition presenting processing is described (STEP S46). Referring to FIG. 27, a circle ○ on the sinusoidal curve stays on the day on which the measurement is made, and it blinks there. At the same time, the message describing the present physical condition such as "PMS" appears and blinks, too. After a while the blinking stops, allowing the word to appear still. The letter, "M" appearing at the lower left and right corners indicates the menstruation period. At STEP S142 the → button sector is depressed, or otherwise, the predetermined length of time has passed, and then, the message which describes the physical condition appears in the display, as shown in FIG. 28. The message contains "Swell level", "Feeling", "Body condition", "Skin condition" and "Pheromone". The "Swell level" is given by the number of reversed marks, each representing one level high. The levels of "Feeling", "Body condition", "Skin condition" and "Pheromone" in "First Period" (Menstruation Period). "Second Period" (Good Condition Period), and "Third Period" (Steady Period) are given in terms of the number of days counted from the beginning of each period. As for the PMS period the levels of "Feeling" and "Body condition" are determined from the swell level, which is determined from the variation of BI values as described at STEP S45. The increase of swell in size indicates the intracerebral edema. Then, the woman may be impatient, and the level of "Feeling" lowers. Also, she feels lassitude, and accordingly the "Body condition" remains at a low level. The "Pheromone" will increase to the maximum level (100%) on the ovulation day. In this particular example these mental or physical conditions are given in the form of bar graphs, but they may be given in the form of circular or line graph or in the form of radar chart. A three-dimensional presentation is possible. After at STEP S143 the → button sector is depressed or otherwise, a predetermined length of time has passed, advisory messages in connection with the physical or mental condition are given, as seen from FIG. 29. At STEP S144 the → button sector is depressed or otherwise, a predetermined length of time has passed, and then, if a decision is made on the pregnancy possibility, the massage is given in the display 42, as seen from FIG. 30. At STEP S 145 the → button sector is depressed or otherwise, a predetermined length of time has passed. Then, the weight and the percent fat are given with indications (↑) and (↓), as seen from FIG. 31. At STEP S146 the → button sector is depressed or otherwise, a predetermined length of time has passed. Then, the display shows the average of the days included in the menstruation cycle each of the previous six months, the average weight, the menstruation cycle beginning and ending days, the number of the days included in the menstruation cycle and the average weight for the menstruation cycle, all counted or calculated in selected menstruation cycle in the past.

Figure 17:
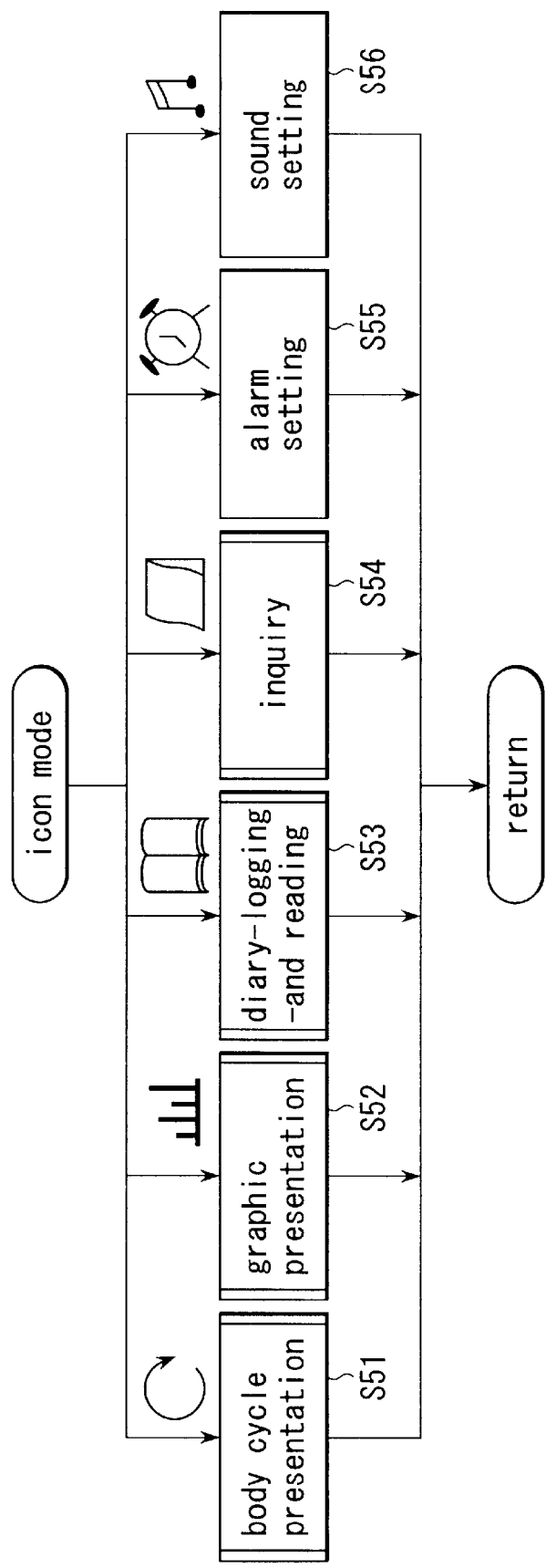
FIG. 17 shows what icons are displayed for selection.

Referring to FIG. 17, icon mode processing (at STEP S6) is described below. First, the body cycle icon (see the top of FIG. 22) is selected by the selection button 41g, and then the decision making button 41f is depressed, allowing the proceeding to advance to STEP S51, at which the processing of body cycle presentation is effected. The graphic presentation icon is selected by the selection button 41g, and then the decision making button 41f is depressed, thereby giving the graphic presentation in the display. The diary logging-and-reading icon is selected by the selection button 41g, and then the decision making button 41f is depressed, allowing the proceeding to advance to STEP S53, at which the diary logging-and-reading is permitted. Likewise, the inquiry icon is selected, and the decision making button 41f is depressed, thereby allowing the proceeding to advance to STEP S54, at which the inquiry is permitted. Now, the alarm setting icon is selected, and the decision making button 41f is depressed, so that the proceeding may advance to STEP S55, at which the required alarm setting is effected. By this processing, the date and time that are famous for alarm sound are set. The sound setting icon is selected by the selection button 41g, and then the decision making button 41f is depressed, thereby allowing the proceeding to advance to STEP S56, at which the sound setting is effected. The on-and-off operation for producing sound other than alarming sound can be set. Some details of each processing are described below by referring to FIGS. 18 to 21.

Figure 18:
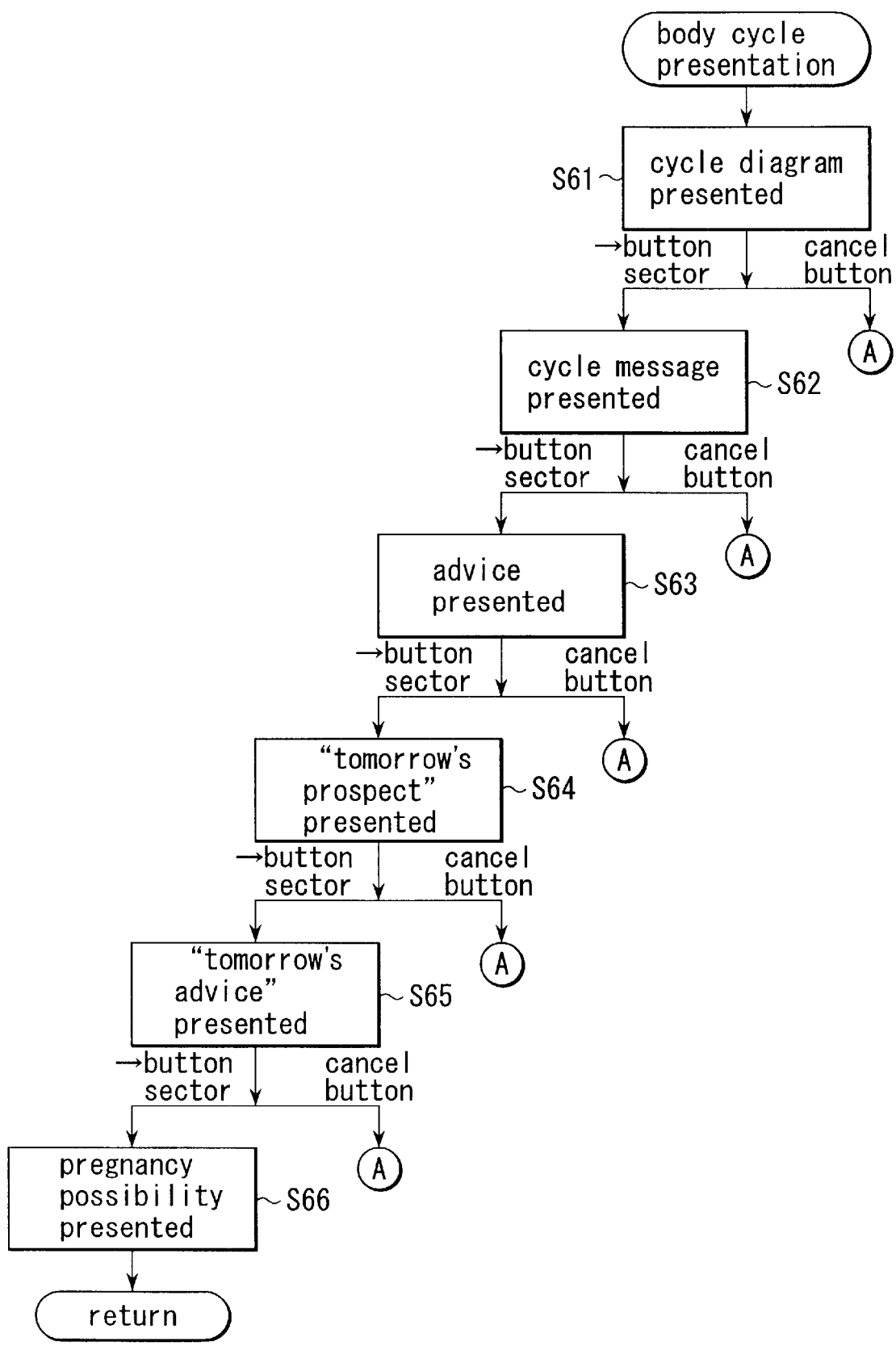
FIG. 18 is a flow chart showing the proceeding by which cyclic body conditions and related advice are given.
Figure 19:
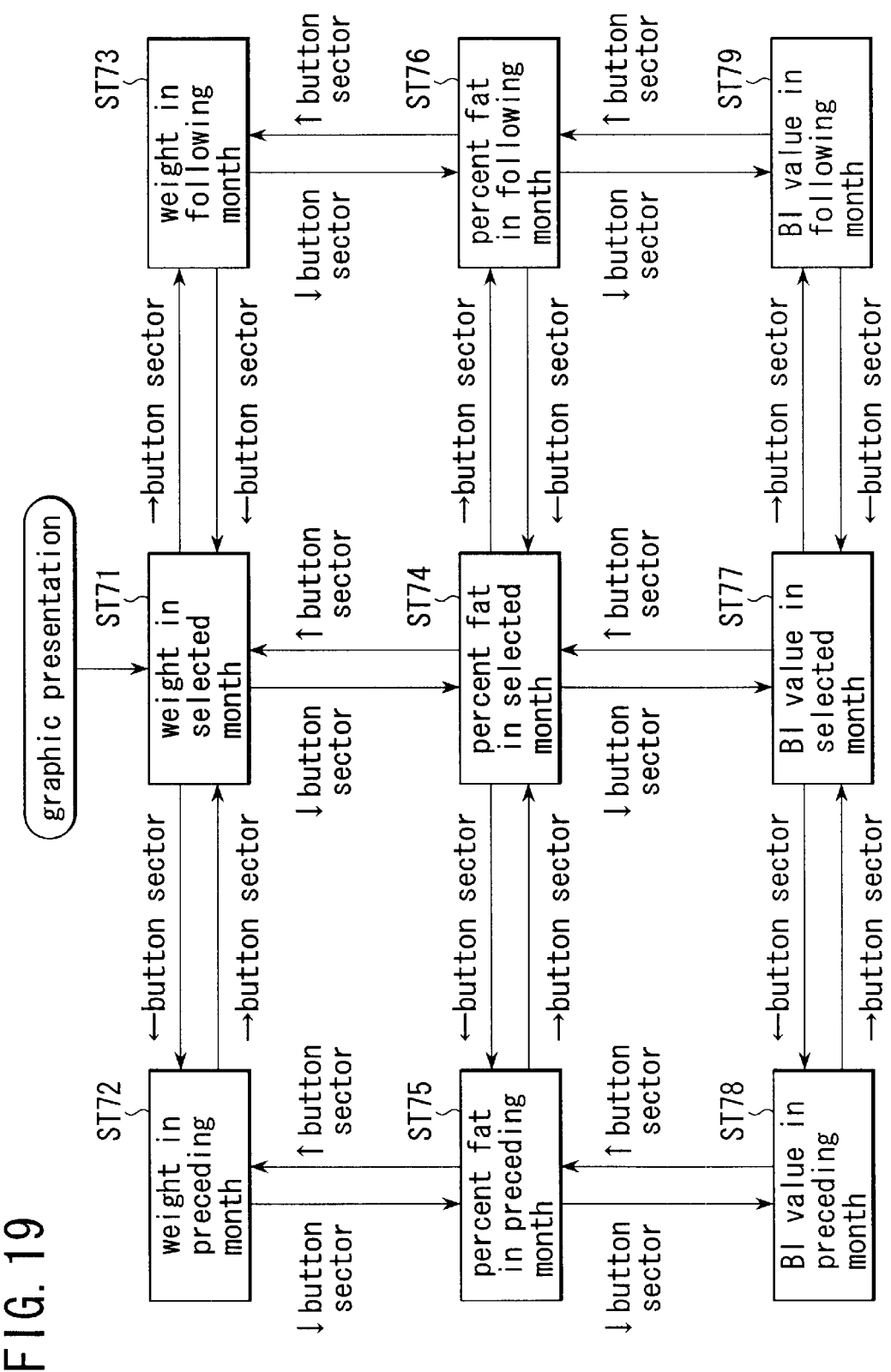
FIG. 19 shows how different items can be transferred from one to another in graphic presentation.
Figures 33, 34:
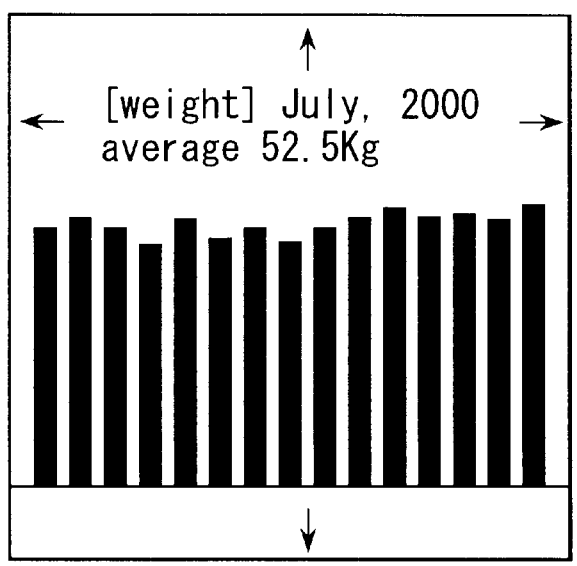
FIG. 33 shows one example of tomorrow's message in the display.
FIG. 34 shows how the weight varies within one month.
Figure 35:
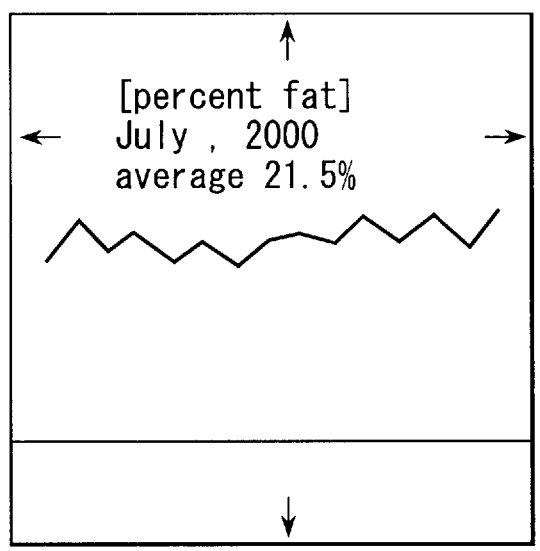
FIG. 35 illustrates how the percent fat varies within one month.
Figure 36:
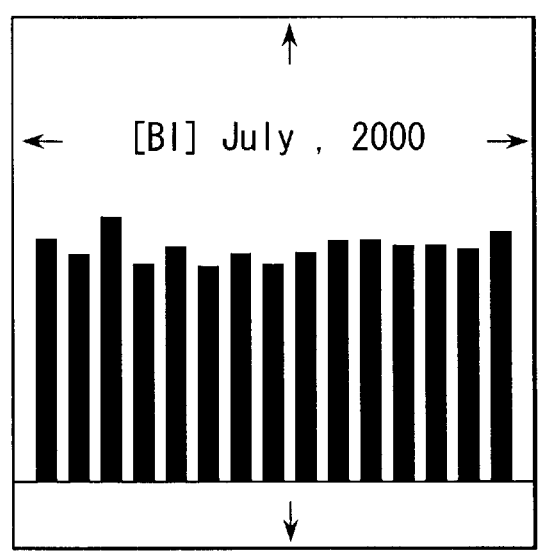
FIG. 36 illustrates how BI values vary within one month.

Referring to FIG. 18, the body cycle presentation processing (STEP S51) is described. The cyclic curve (see FIG. 27) appears as is the case with STEP S141 (see FIG. 16). When the cancel button is depressed, the proceeding returns to STEP S3. The → button sector is depressed or otherwise, a predetermined length of time has passed. As is the case with STEP S142, the cycle message appears (see FIG. 28) as described at STEP S142. Depression of the cancel button permits the proceeding to return to STEP S3. The → button sector is depressed or a predetermined length of time has passed. As is the case with STEP S143, advice messages (see FIG. 29) are given at STEP S63. Depression of the cancel button permits the proceeding to return to STEP S3. The → button sector is depressed or a predetermined length of time has passed. Then, the "Tomorrow's Prospect" message appears at STEP S64. Depression of the cancel button permits the proceeding to return to STEP S3. The → button sector is depressed or a predetermined length of time has passed. Then, the Tomorrow's Advice messages (FIG. 33) are given at STEP S65. Depression of the cancel button permits the proceeding to return to STEP S3. In a case where a decision is made on the pregnancy possibility, the → button sector is depressed or a predetermined length of time has passed. Then, the woman is informed of the possibility of being pregnant (FIG. 30) at STEP S66, as is the case with STEP S144.

Referring to FIG. 19, the graphic presentation processing (STEP S52) is described. The graph given in the STATE ST71 shows the variation of the weight in a selected month and the average weight (see FIG. 34). Depression of the ← button sector makes the presentation transfer to the STATE ST72, where the variation of the weight in the preceding month and the average weight are shown. Depression of the → button sector makes the presentation transfer to the STATE ST71. Other state transfers equally, too. In the STATE ST73 the variation of the weight in the following month and the average weight are shown. In the STATE ST74 the variation of the percent fat in the selected month and the average percent fat are shown. In the STATE ST75 the percent fat in the preceding month and the averagee percent fat are given. In the STATE ST76 the variation of the percent fat in the following month and the average value are given. In the STATE ST77 the graphic presentation of BI values in the selected month and the average value are given. In the STATE ST78 the graphic presentation of BI values in the preceding month and the average value are given. In the STATE ST79 the graphic presentation of BI values in the following month and the average value are given. A predetermined length of time has passed without depressing the → or ← button sector, and then, the power supply is made to turn off.

Figure 20:
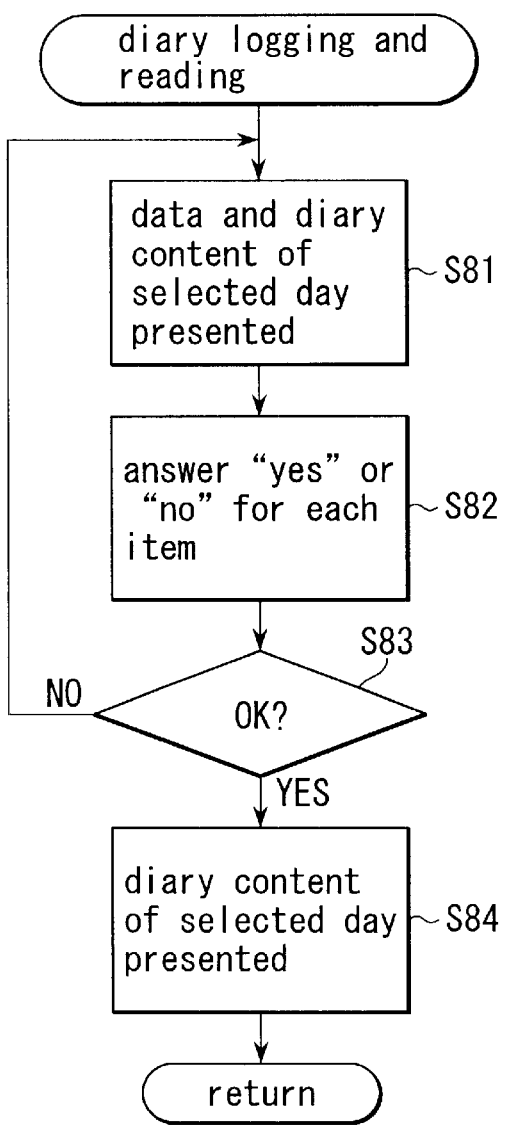
FIG. 20 is a flow chart showing the proceeding by which a diary is logged and read.
Figure 39:
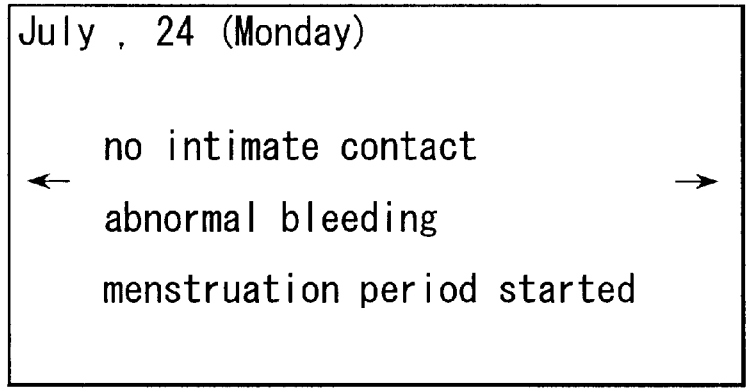
FIG. 39 shows the diary content of the day in question.
Figure 40:
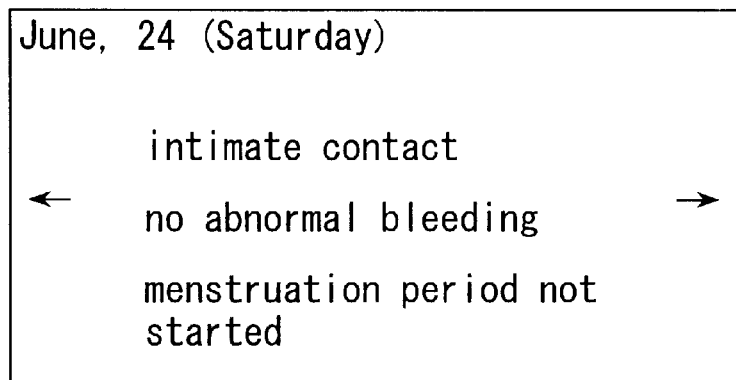
FIG. 40 shows the diary content of the day in question in the previous month.

Referring to FIG. 20, the diary logging-and-reading processing (STEP S53) is described. At STEP S81 a selected date and the diary page of the selected date appear in the display 42, as seen from FIG. 37. At STEP S82 the woman answers each question by selecting YES or NO. In selecting YES the ↑ button sector is depressed, and then, the decision making button 41f is depressed. In selecting NO the ↓ button sector is depressed, and then, the decision making button 41f is depressed. Desired entry in the selected previous diary page (or backlogging) may be permitted by using the ← button sector. When the cancel button is depressed, the proceeding returns to STEP S3. At STEP S83 a confirmation screen appears, as seen from FIG. 38. The woman can say, "YES" or "NO" by pushing the ↑ button sector or ↓ button sector, and by pushing the decision making button 41f. When "NO" is selected, the proceeding returns to STEP S81. At STEP 84 the selected diary page appears (see FIG. 39). When the ← button sector is depressed, another selected diary page is shown (see FIG. 40). Depression of the → button sector makes the proceeding go back.

Figure 21:
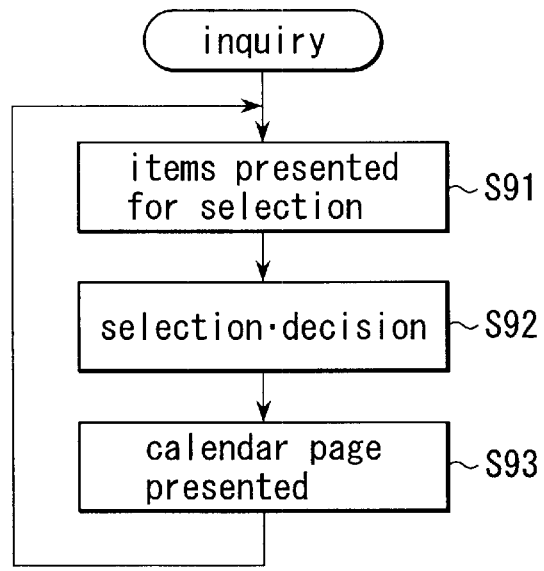
FIG. 21 is a flow chart showing the proceeding by which an inquiry is made.
Figures 41, 42:
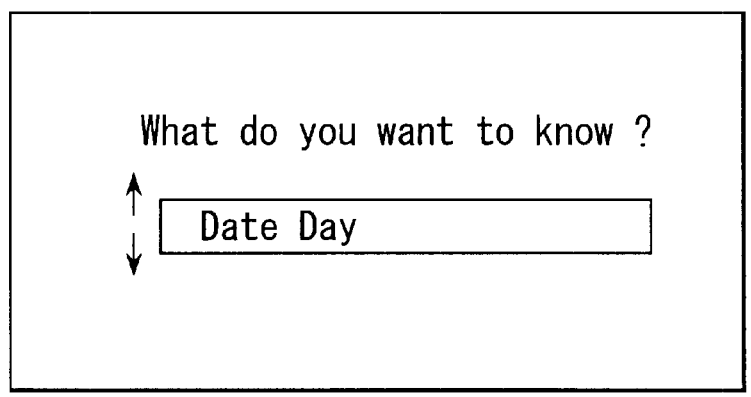
FIG. 41 shows an inquiry making screen.
FIG. 42 shows which days are Date Days.

Referring to FIG. 21, an inquiry processing(STEP S54) is described. At STEP S91 a message which reads "What do you want to know ?" appears along with some items to be selected, as shown in FIG. 41. At STEP S92 the woman pushes the ↑ button sector or the ↓ button sector to scroll, and then the decision making button 41f is depressed. Examples of the items to be selected are: "Date Day", "Abnormal Bleeding Day", "Beginning Day of Menstruation Period", "Beginning Day of Next Menstruation Period", "Ovulation Day and Expected Date of Becoming Pregnant", "Expected Day of Next PMS", "Suitable Day of Dieting" and such like.

"Suitable Day (Period) of Dieting" can be determined as follows: the "Period" starts three days earlier than the expected Ovulation Day. Assuming that the woman's menstruation cycle has 28 days. The "Period" starts three days earlier than the fourteenth day from the day the menstruation is depressed. As a matter of course the start of the "Period" depends on the average menstruation cycle of the woman in question.

The swell disappears before the ovulation day, and the woman grows slim more or less while the body temperature has not risen yet. It is said that while the woman's body remains in such condition, the dieting can be effectively performed by taking care of food and exercise.

Termination of the "Period" is determined as follows: the BI curve descends to level off. The "Period" terminates on the fourth day counted forward from the beginning of the leveling-off period. Stated otherwise, the "Suitable Day of Dieting (Period)" terminates on the fourth day from the rise of the body temperature. The reason is that the consumption of energy increases while the body temperature remains at a high level.

At STEP S93 there appears the calendar page containing the day selected at STEP S92, which day blinks. Alternatively only the selected date may be displayed with character. Depression of the → button sector makes the proceeding return to STEP S91. Otherwise, if a predetermined length of time has passed, the proceeding returns to STEP S91. Depression of the cancel button 41h makes the proceeding return to STEP S3.

Figure 11:
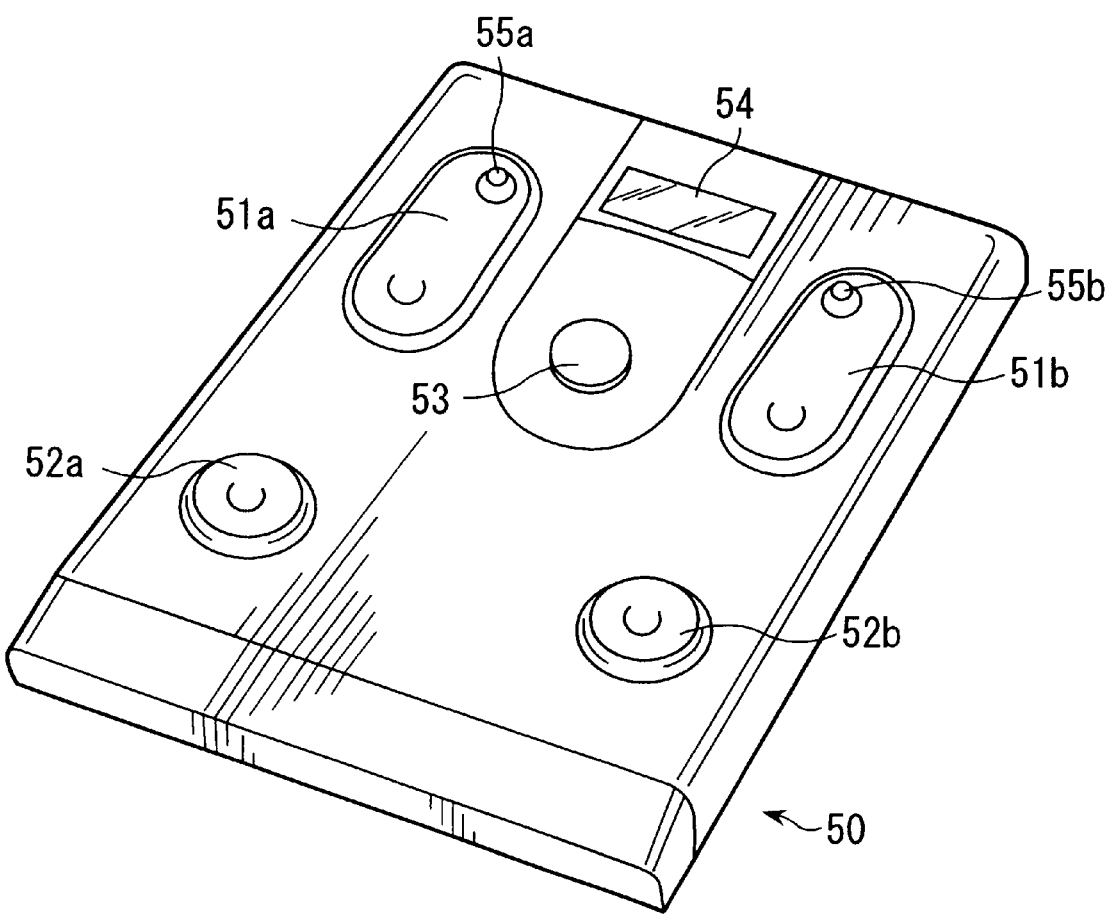
FIG. 11 is a perspective view of a female physical condition managing apparatus according to a second embodiment of the present invention.

Referring to FIG. 11, a female physical condition managing apparatus 50 according to the second embodiment has a scale-and-bioelectrical impedance meter and a control box both combined as a whole, and is capable of measuring the body temperature of the user. In these respects the apparatus 50 can be distinguished from the first embodiment of FIG. 9. The female physical condition managing apparatus 50 has constant current feeding electrodes 51a and 51b, voltage measuring electrodes 52a and 52b, an operating push button 53 and a display 54 arranged on its front. Body temperature measuring sensors 55a and 55b are placed at the upper parts of the constant current feeding electrodes 51a and 51b. These sensors 55a and 55b are so constructed that they may be pinched between selected fingers of both feet. Alternatively an ear measuring type of infrared thermometer may be connected to the female physical condition managing apparatus 50. A sublingual type of thermometer may be connected for precision measurement. The body temperatures thus measured can be used along with BI values for the CPU to make a decision on the women's monthly physical condition. Therefore, precision decision of the physical condition can be performed.

The female physical condition managing apparatus according to the first and second embodiments are so constructed that BI appearing between both hands or between one hand and one foot may be measured.

A selection button may be provided for selecting individual personal data among those stored in the memory, so that the apparatus may be used by two or more women in common.

It may be possible that the percent fat be determined from the measured BI values, and that the so determined percent fat be given in the display. On the basis of the body temperature and weight thus determined a decision can be made on the woman's periodic physical condition. These data may be given in the display.

Figure 43:
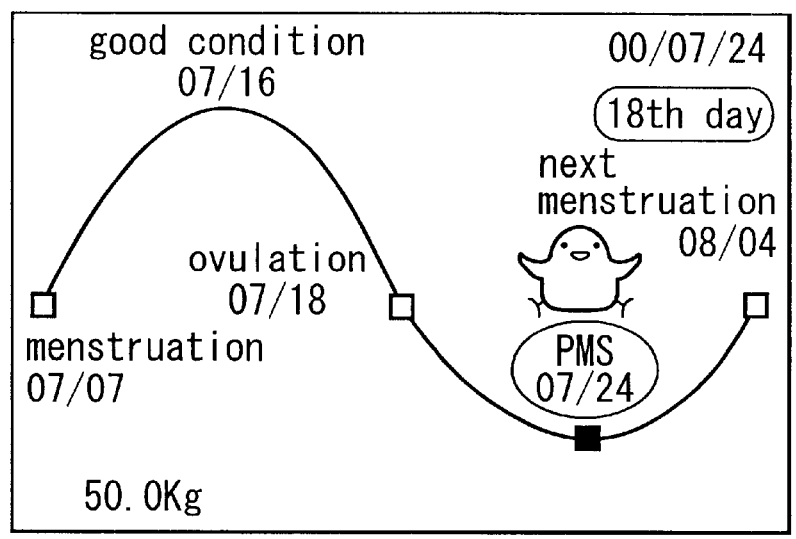
FIG. 43 illustrates the practice of the decisions being given in the display.

Referring to FIG. 43, the display of FIG. 27 is modified as shown in FIG. 43 according to another embodiment. The circular mark ○ stays on the day in question, blinking and encircling a message describing the present day's physical condition, as is in FIG. 27. In this particular embodiment the physical conditions on other specified days are shown along with the dates. Examples of such physical conditions are menstruation, "good condition" period, ovulation and next menstruation. A chick appears on the position at which the present day's physical condition is described. The weight appears on the lower, left side.

Figure 26:
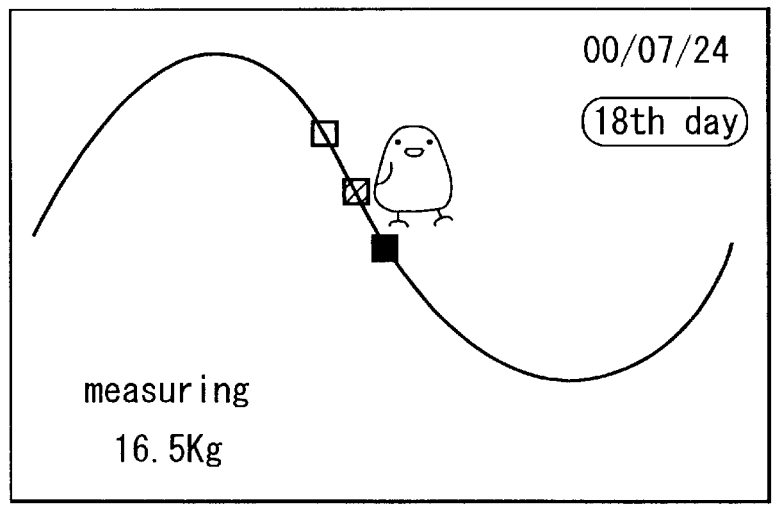
FIG. 26 illustrates a screen appearing in the display during the measurement.
Figure 44:
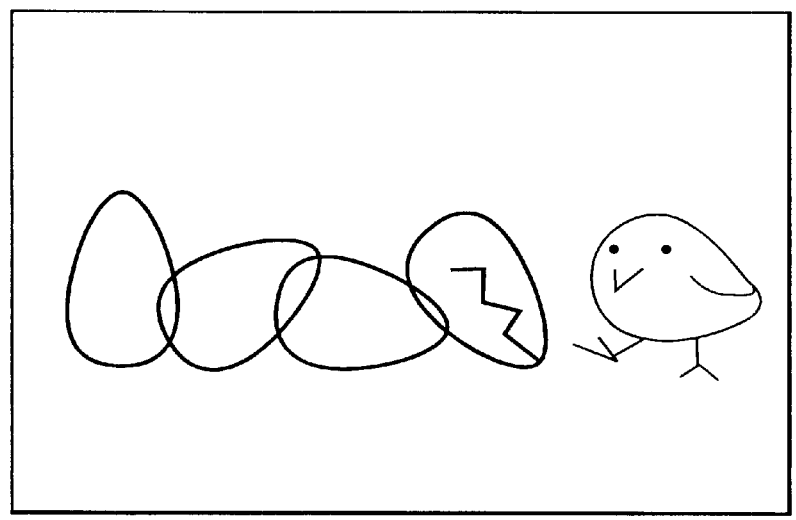
FIG. 44 illustrates animation-like figures appearing in the display while a required measurement is being made.

Referring to FIG. 44, the display of FIG. 26 is modified as shown according to still another embodiment. While measuring and making a decision on a selected subject an egg is rolling rightward, and the egg break. A chick appears from the broken egg just before termination of the decision-making. This animation may be replaced by a monthly incidence such as the transition from the crescent to full moon.

Referring to FIGS. 45 to 51 another practice of making a required measurement and decision on women's physical condition is described below.

Figure 45:
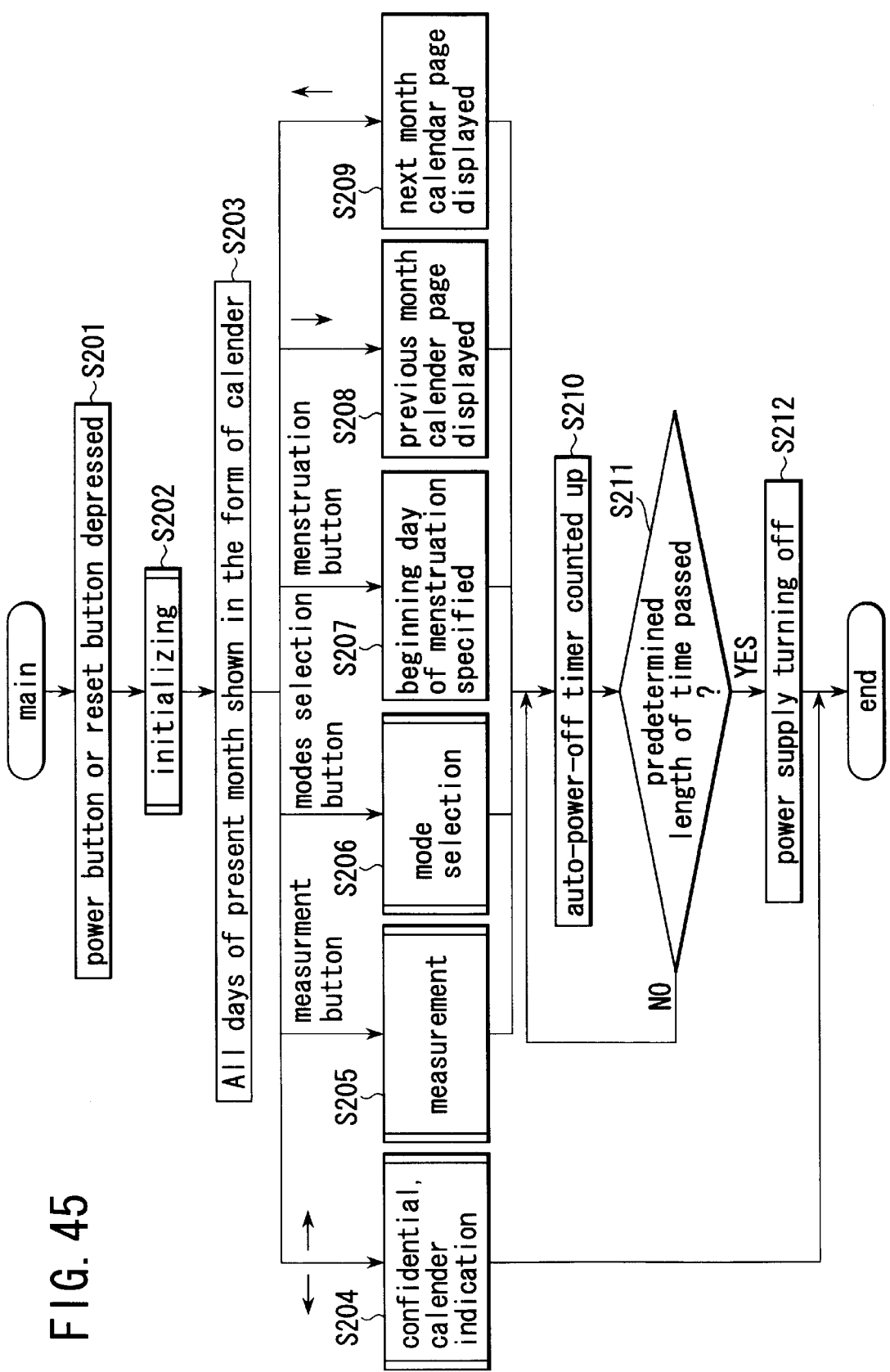
FIG. 45 is a flow chart showing the proceeding by which a decision is made on the monthly physical condition.

FIG. 45 shows the main program according to which the female physical condition managing apparatus works. First, referring to FIG. 45, the power button 41a (see FIG. 9) is depressed at STEP S201, thereby putting the apparatus in circuit with the power supply. Then, the apparatus is initialized at STEP S202 as later described in detail. All the days of the present month are shown in the form of calendar in the display 42 at STEP S203 (see FIG. 52). In the calendar display the FIG. 30 is reversed to indicate the present day.

By depressing the ← button sector or → button sector of the direction button 41j, the measurement button 41b, the selection button 41e, the menstruation button 41e or the ↓ button sector and ↑ button sector of the direction button 41j (see FIG. 9), S204, S205, S206, S207, S208, or S209 is executed, respectively.

At STEP S204 the apparatus works in the confidential calendar indication mode, in which the delicate period of menstruation, the dieting period appropriate for going on a diet, pre- and post-ovulation period for getting pregnant with ease, PMS preventing period for precautionary nursing and the PMS period, these being indicated on a selected page or pages of the calendar, as later described in detail. At STEP S205 the apparatus works in the measurement mode in which: BI value and other factors are determined; and the results of the measurements are displayed, as later described in detail. At STEP S206 the apparatus carries out the proceeding in a selected mode. Some details are described later.

At STEP S207 the beginning day of the menstruation period is specified on the calendar page. At STEP S208 the page of the previous month of the calendar appears on the screen. At STEP S209 the page of next month of the calendar appears on the screen.

At STEP S210 the auto-power-off timer is counted up. The auto-power-off timer is reset in response to the turning-on of the power supply or to the key depression. At STEP S211 a decision is made as to whether the predetermined length of time has passed. In the negative the proceeding returns to STEP 210. In the affirmative the power supply is made to turn off at STEP S212.

Figure 46:
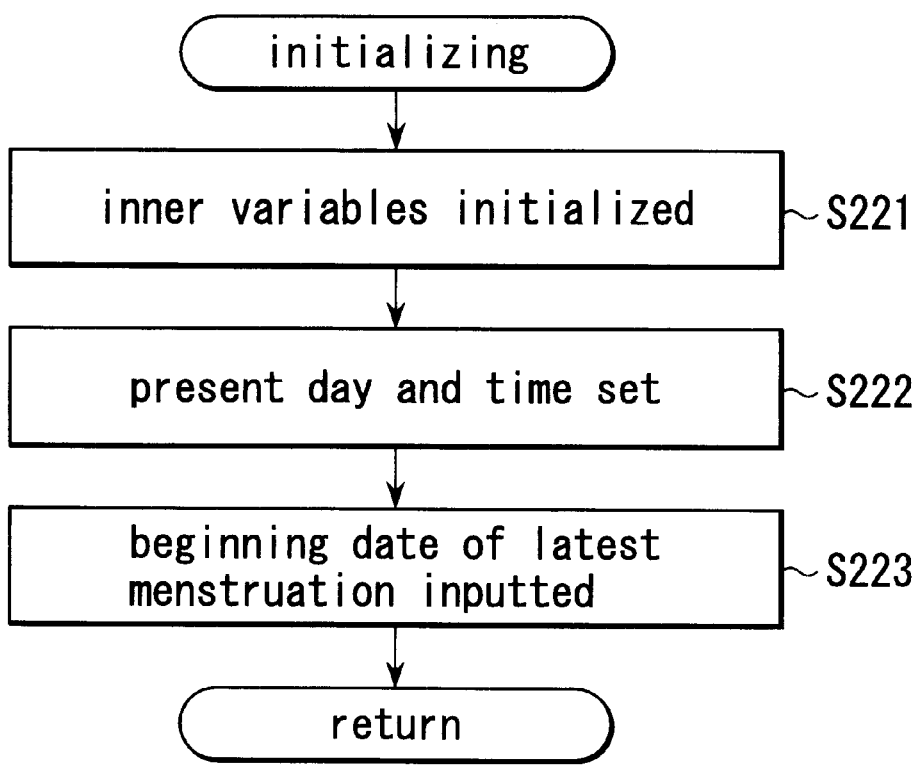
FIG. 46 is a flowchart according to which the initialization is made.

Referring to FIG. 46, the initializing process (STEP S202) can start in response to depression of the power supply button or the resetting button. As described earlier, initialization is necessitated provided that the power supply turns on for the first time. A decision can be made as to whether the power supply has turned on before (in the affirmative case no initialization required) by checking whether an initializing flag has been set or not. In the affirmative no initialization is required.

At STEP S221 initialization is effected on each and every inner variable. At STEP S222 the inner clock is set for the present day and time. At STEP S223 the beginning day of the latest menstruation period and the number of the days included in the menstruation cycle are inputted.

Figure 47:
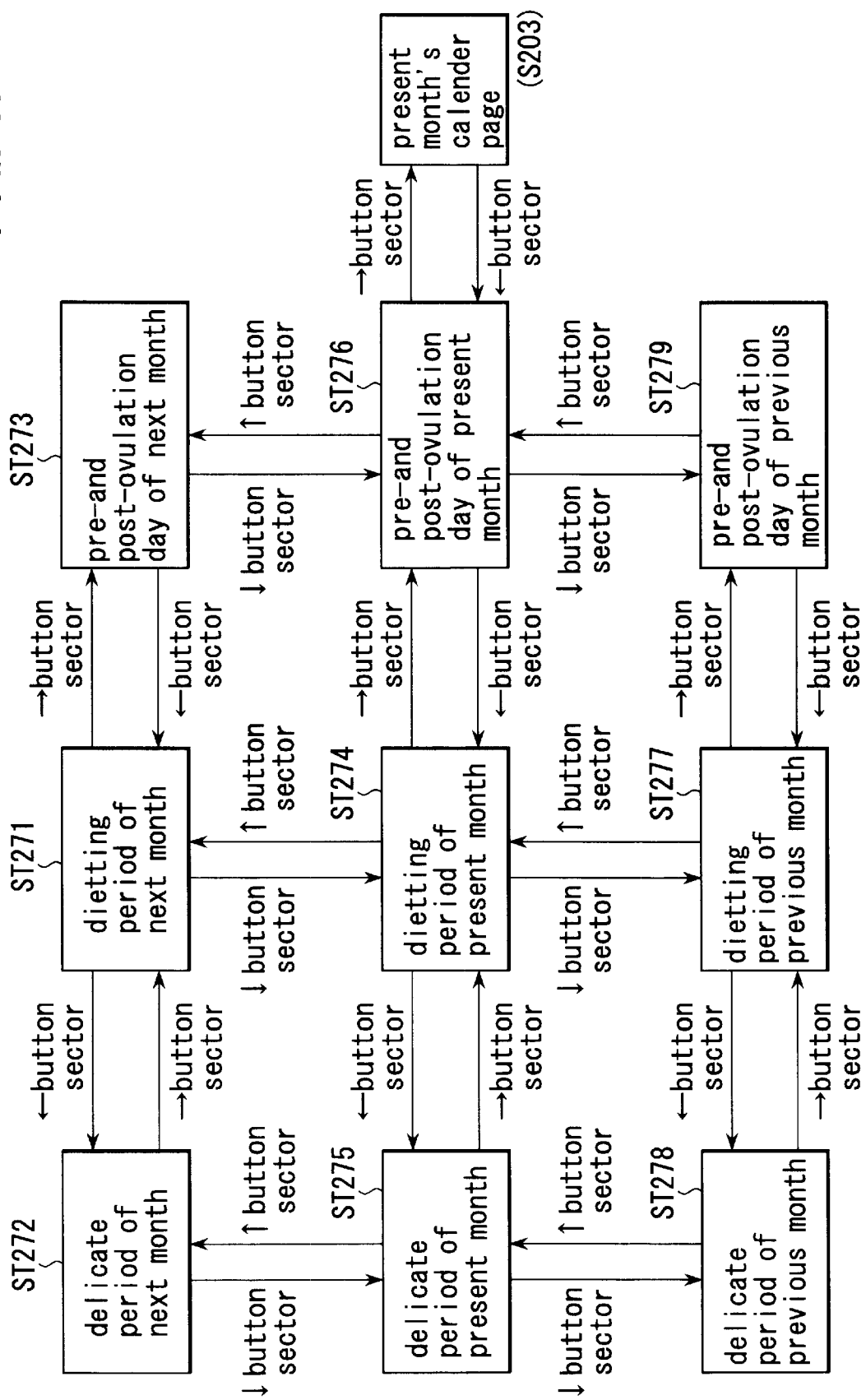
FIG. 47 illustrates how selected graphic presentations can be changed one after another.
Figure 53A:
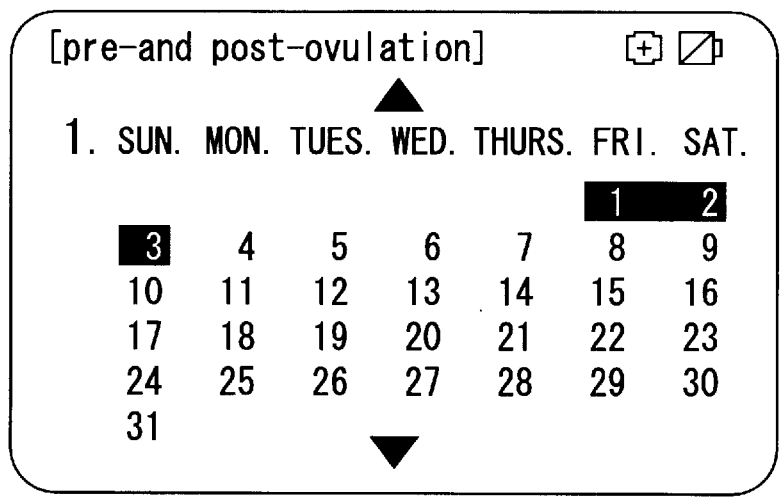
FIGS. 53a, 53b, and 53c show confidential presentations in the form of calendar.
Figure 53B:
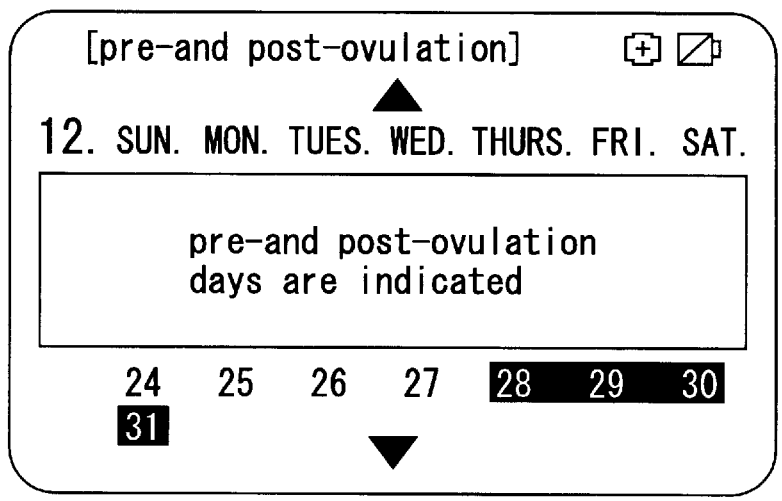
Figure 53C:
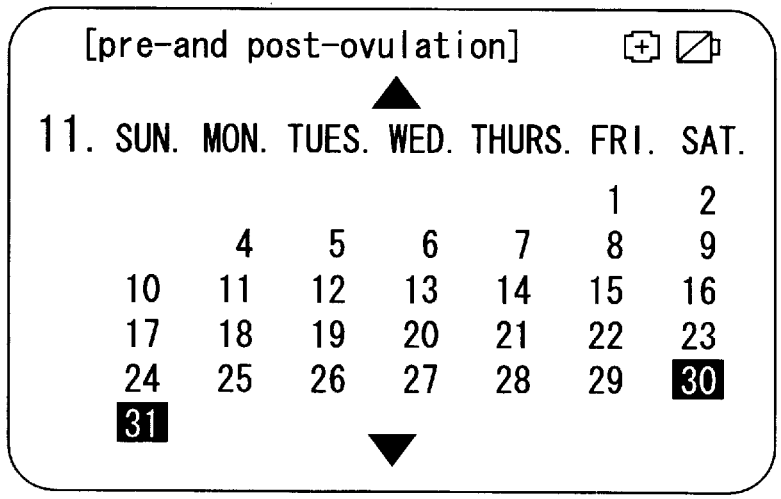

Referring to FIG. 47, the confidential, calendar indication processing (STEP S204 in FIG. 45) is described. Because of the nature of secrecy use is made of no icon representing the handling of matters of secrecy. Referring to FIG. 45, the page of the calendar showing all days of the present month (for example, December) is made to appear in the display (STEP S203). Depression of the ← button sector makes the presentation transfer to the STATE ST276, where the message reading "pre- and post-ovulation days are indicated" appears in the display 42, making these days to be reversed and blinked as shown in FIG. 53b. In this position depression of the ↑ button sector makes the presentation transfer to the STATE ST273, where pre- and post-ovulation days of next month (for example, January) are indicated by reversing and blinking these days in the calendar page as shown in FIG. 53a. While remaining at STEP ST276, depression of the ↓ button sector makes the presentation transfer to the STATE ST279, where pre- and post-ovulation days of the previous month (for example, November) are indicated by reversing and blinking these days in the calendar page as shown in FIG. 53c. In the STATE ST274 the dieting period appropriate for going on a diet for the present month is given by reversing and blinking the days of the dieting period in the calendar page. Depression of the ← button sector makes the presentation transfer to the STATE ST275, where the days of the delicate period for the present month are indicated by reversing and blinking these days in the calendar page. In this position depression of the → button sector makes the presentation return to the STATE ST274. In the STATE ST271 the dieting period of next month is given. In the STATE ST272 the delicate period of next month is given. In the STATE ST277 the dieting period of the previous month is given. In the STATE ST278 the delicate period of the previous month is given. A predetermined length of time has passed without depressing the →, ←, ↑ or ↓ button sector, and then, the power supply is made to turn off.

Figure 48:
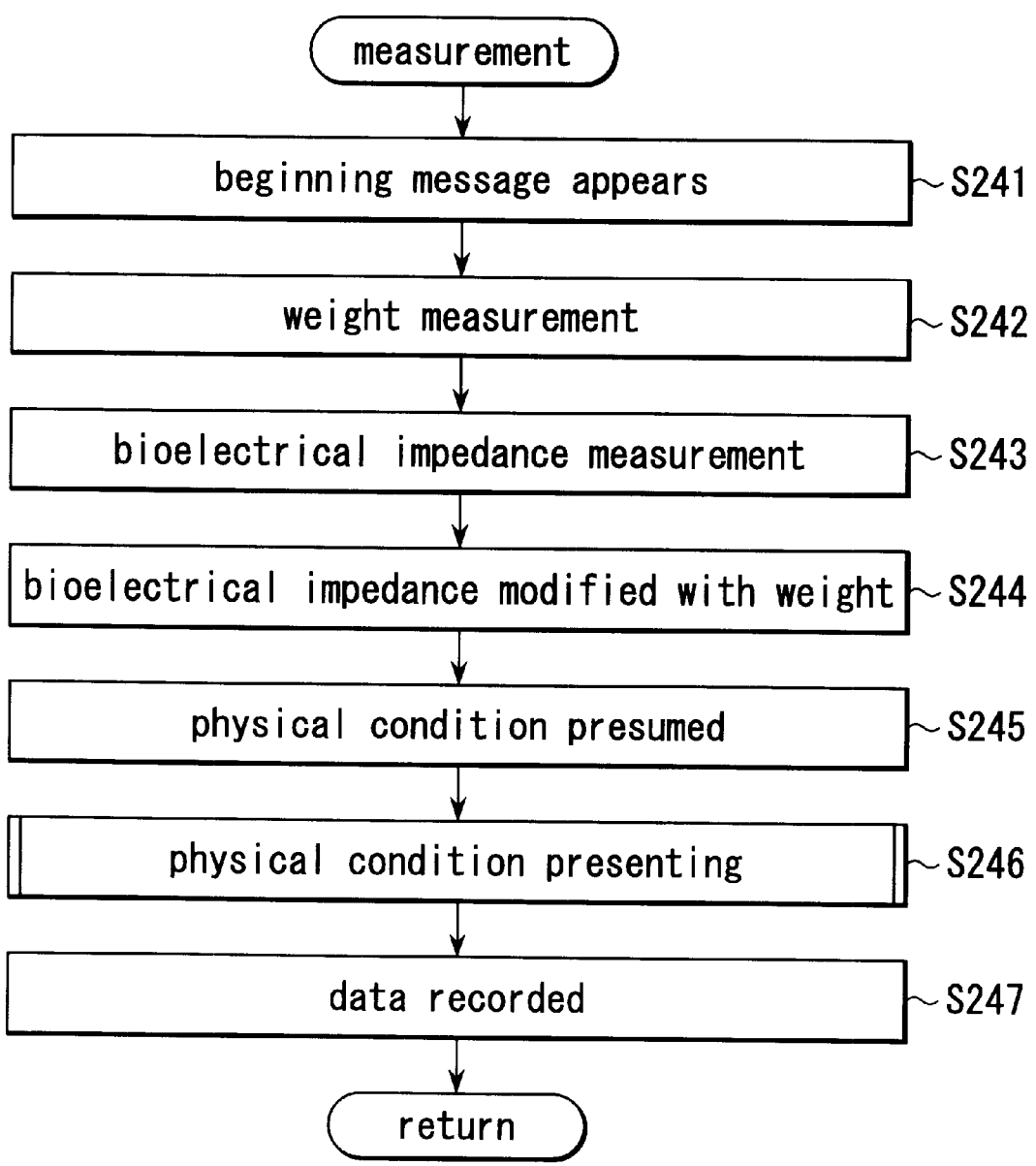
FIG. 48 is a flow chart showing a series of steps for measurement.
Figure 54:
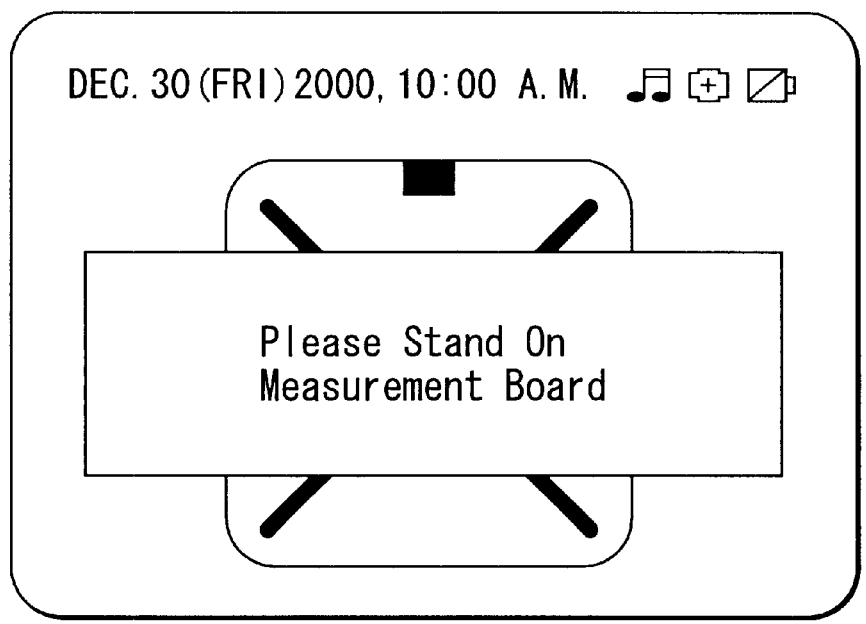
FIG. 54 shows a message appearing in the display at the outset of measurement.

Referring to FIG. 48, some detail of the measurement processing (STEP 205 in FIG. 45) is described. At STEP S241 a message reading "Please stand on measurement board" appears and blinks in the display 42, as seen from FIG. 54. At the same time the day and time appear at the head of the display 42. When the cancel button 41h is pushed, the proceeding returns to STEP S203.

Figure 55:
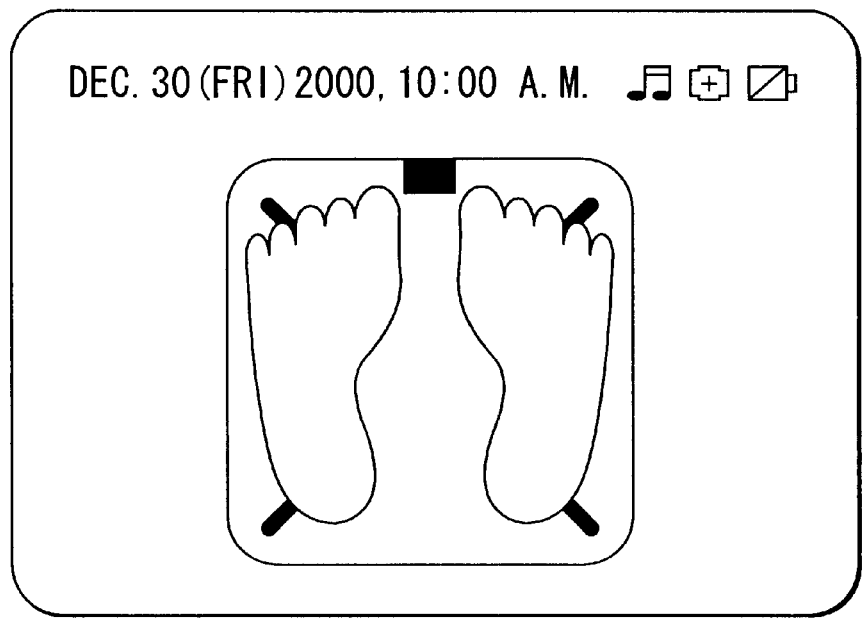
FIG. 55 shows an image of footprints to indicate where the user's feet are put on the measurement board.
Figure 56:
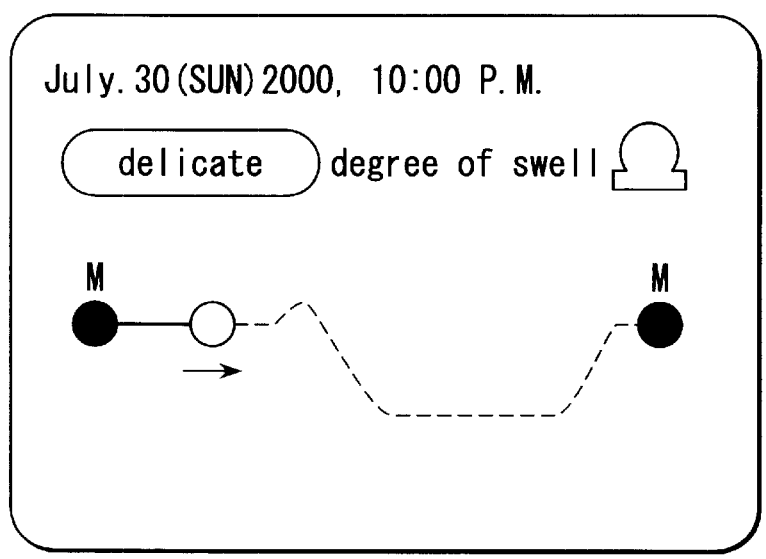
FIG. 56 shows an image appearing in the display during measurement.
Figure 57:
FIG. 57 shows a series of varying figures representing different degrees of swell.

At STEP S242 the footprints appear and blink in the display 42 for a while to indicate how the user stands on the weight-and-bioelectrical impedance meter 20 (see FIG. 55). Within 30 seconds she is requested to stand on the weight-and-impedance meter with the toes and heels of the left and right bared feet put on the constant current feeding electrodes 21a and 21b and the voltage measuring electrodes 22a and 22b respectively. Now, the weight measuring unit 25 detects her weight, and the measurement starts with weighing her weight. At STEP S243 the bioelectrical impedance measurement is made as follows: the high-frequency, constant current circuit 23 makes a high-frequency, weak current flow in her body via the constant current feeding electrode 21a, the toe of the left foot, the left leg, the lower part of her abdomen, the right leg, the toe of the right foot and the constant current feeding electrode 21b. The voltage measuring circuit 24 determines the voltage appearing between the voltage measuring electrodes 22a and 22b, thus determining the value of BI. The CPU 45 allows the display 42 to show a BI transition symbolic curve as seen from FIG. 56 until the measurement result is displayed. The BI transition symbolic curve symbolizes the variation of BI values from the menstruation to the next menstruation, allowing the circle ○ to move from left to right once cyclically in five or six seconds. In synchronism with the movement of the circle, the words identifying the period such as "delicate" or dieting appears. In synchronism with the movement of the circle the indication of the degree of swell (see FIG. 57) appears at the upper, right corner of the display. This has the effect of lessening the boredom which the user may feel while waiting for the result of measurement. Also, the woman can learn from the transition symbolic curve how the BI value will vary from the menstruation to the next menstruation. Specifically she can realize that five periods appear one after another from the names of these periods, which appear in sequence while the circle is moving on the BI transition symbolic curve. Likewise, symbolic simulations of swell appear so that the woman may realize in which period the swell may appear. At STEP S244 the value of BI determined is modified with weight to provide the weight-modified BI value, which is free of the effect caused by the weight on the measured BI value.

At STEP S245 the present physical condition is determined in consideration of the monthly female physical condition-and-BI relationship. The required determination can be made on the basis of the present weight-modified BI (which is determined at STEP S244), the previous weight-modified BI (which is retrieved from the memory 24) and data collected for the menstruation cycle (which is retrieved from the memory 24) as follows:

the first week starting from the beginning day of the menstruation specified at STEP S207 is done with delicate period. The second period is done with dieting period, starting from the day subsequent to the termination of the delicate period and ending with the day previous to the day on which a BI value is measured 4% lower than the average BI value of the second week in the previous monthly record. The third period is done with PMS preventing period, starting from the day subsequent to the termination of the second or dieting period and ending with the day one week earlier than the beginning day of the menstruation, which beginning day can be presumed from the record. Finally, the fourth period is done with PMS period, starting from the day subsequent to the termination of the third or PMS preventing period and ending with the day on which data pertaining to the beginning day of next menstruation are inputted. A decision is made as to which change appears, Type A, B or C in FIG. 7 to determine whether the PMS has appeared. Specifically the change of Type A indicates that the user has a PMS.

The presumable ovulation day falls on the fourteenth day counted backward from the beginning day of next menstruation presumable from the record. The ovulation day is the last day of the dieting period, and therefore, if the ovulation day should fall on the next day, the possible pregnancy day needs to be corrected accordingly. The fifth period is composed of the five days including the ovulation day and two days before and after the ovulation day, and is done with "pre- and post-ovulation" period.

The decision making as above described requires the past record of data, which was made at least one month previous to the decision making. In a case where no prior record is available, the message which reads "Today physical condition cannot be displayed because required data is unavailable" appears in the display 42.

Now, the manner in which a decision is made as to whether or not the swell characteristic of the PMS period appears is described below. The average value of BI is determined from those recorded for a selected PMS period in the past, and the so determined average value of BI is used as the STANDARD. Specifically the degree of swell is determined as SWELL LEVEL 1 when the value of BI decreases 1% down with respect to the STANDARD, and the degree of swell rises one level high each time the value of BI has decreased 1%.

At STEP S246 the measurement and decision is completed normally to show the physical condition presumed in the display, as later described in detail. At STEP S247 the → button sector is depressed, or otherwise, a predetermined length of time has passed, and then, the message which reads "Push the record button to record the data." appears in the display. The record button 41c is depressed to store in the memory 44 the weight-modified BI value and the weight, both of which are determined this time. The proceeding returns to the main program.

Figure 49:
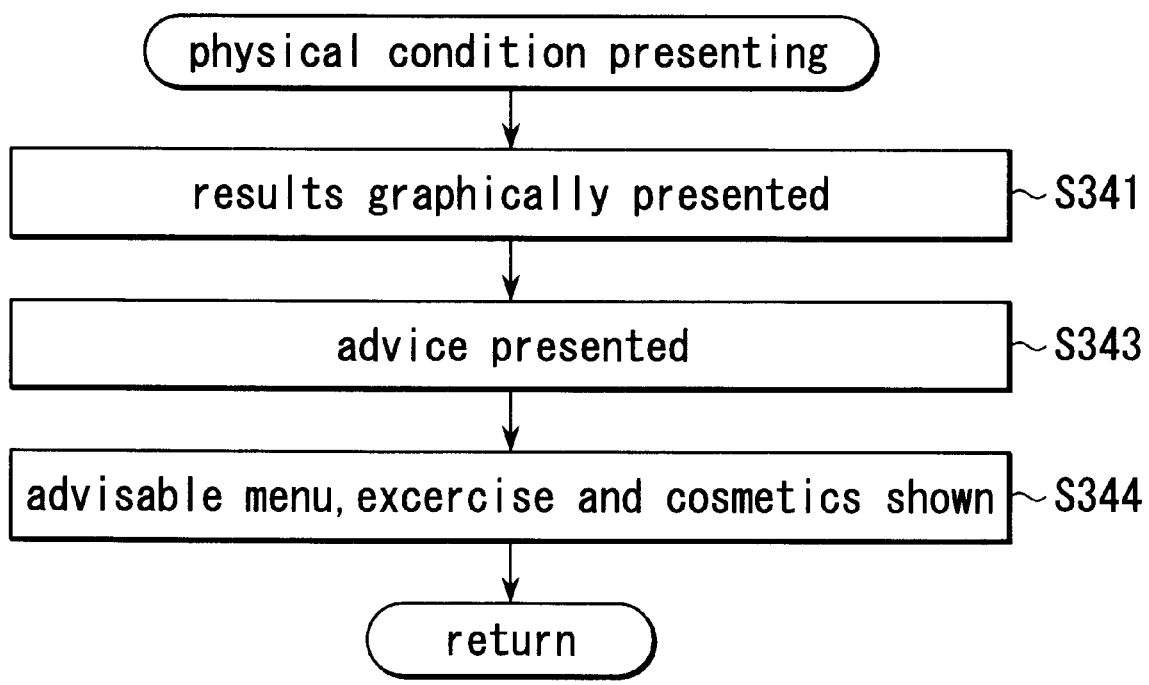
FIG. 49 is a flow chart showing a series of displays for the physical condition.
Figure 58:
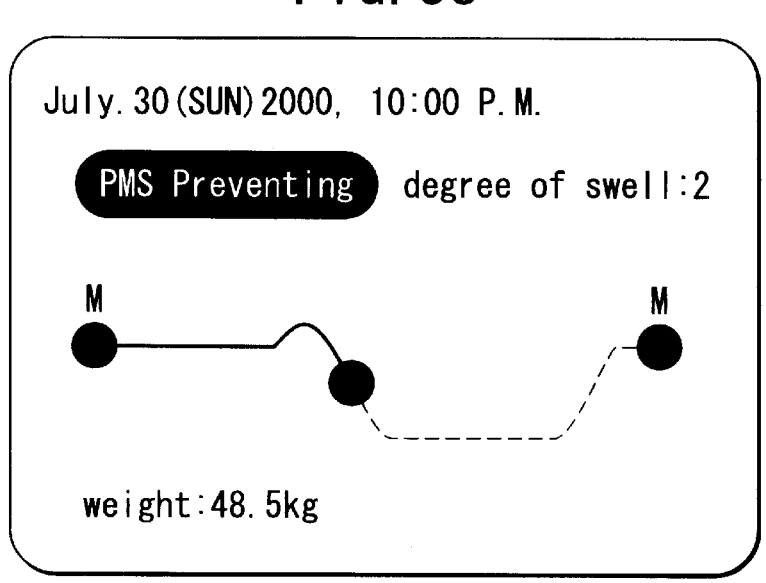
FIG. 58 illustrates an image showing the results of a decision made on the physical condition.

Referring to FIG. 49, the physical condition presenting processing is presented is described (STEP S246 in FIG. 48). Referring to FIG. 58, a BI transition symbolic curve has a black circle ● staying and blinking at a position corresponding to the day on which the measurement is made, and at the same time, the name of the period of physical condition, that is, "PMS preventing" appears and blinks. The letter, "M" is the initial of "menstruation". At STEP S343 the → button sector is depressed, or otherwise, a predetermined length of time has passed, and then, the advisory message appears in the display as shown in FIG. 59. The period name of physical condition "PMS Preventing" is shown. The example of advisory message for PMS preventing is "PMS coming soon. Your condition will soon become unstable, so you should be prepared to maintain a positive way of thinking. Thus, the user is warned to prepare for the coming PMS, and she can learn how to deal with such unstable medical and physical condition without consulting medical books: it would take her much time to find the answer in medical books even though available somewhere. The degree of swell is given alternately in terms of graphic and digital presentations in the display 42. The weight is indicated at the lower part of the display. At STEP S344 the → button sector is depressed, or otherwise, a predetermined length of time has passed, and then, the names of recommendable exercise and food and the cosmetic manner are given. In FIG. 60 stretch and pumpkin are given as recommendable. For the delicate period the advisory message, such as "Light make up.", is given.

Figure 61:
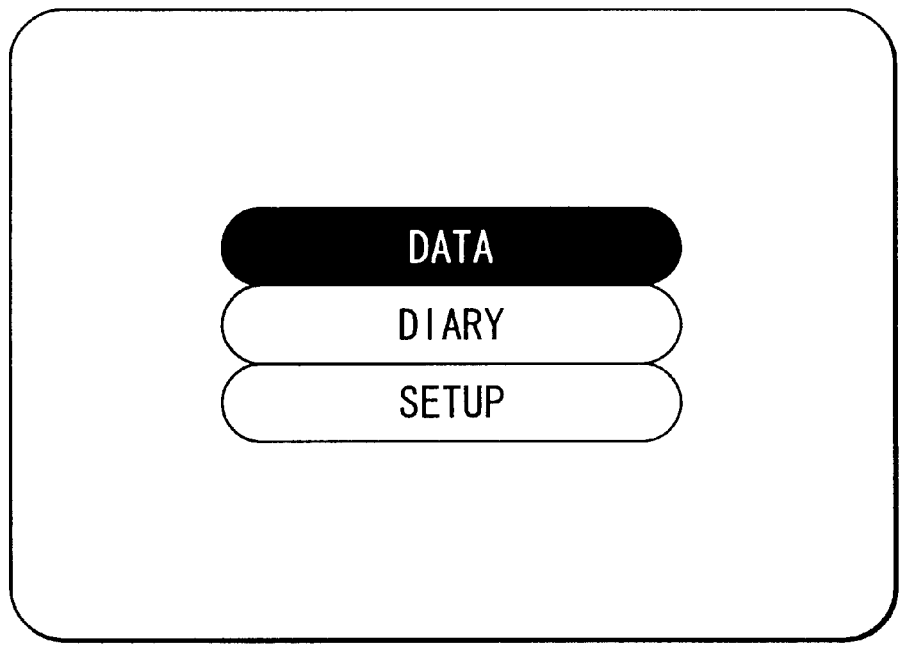
FIG. 61 shows an image for selecting a desired mode among those appearing in the display.

Next, the mode selection processing (STEP S206), which is selected by depressing the mode selection button 41*g*, is described in detail. Referring to FIG. 61, the names of modes to be selected appear in the display in response to depression of the mode selection button 41*g*. A desired mode can be selected by using the ↑ or ↓ button sector. The so selected mode is reversed. The proceeding starts when the decision button 41*f* is depressed. By way of example the DATA MODE is selected.

Figure 50:
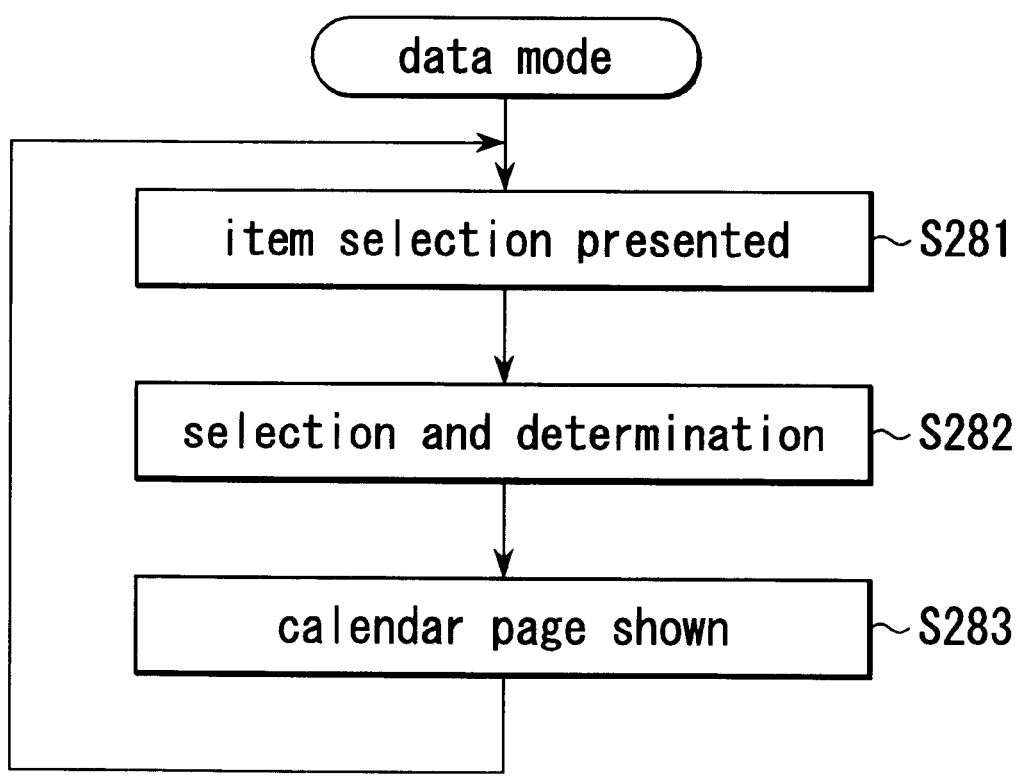
FIG. 50 shows a series of steps in the data mode.
Figure 62:
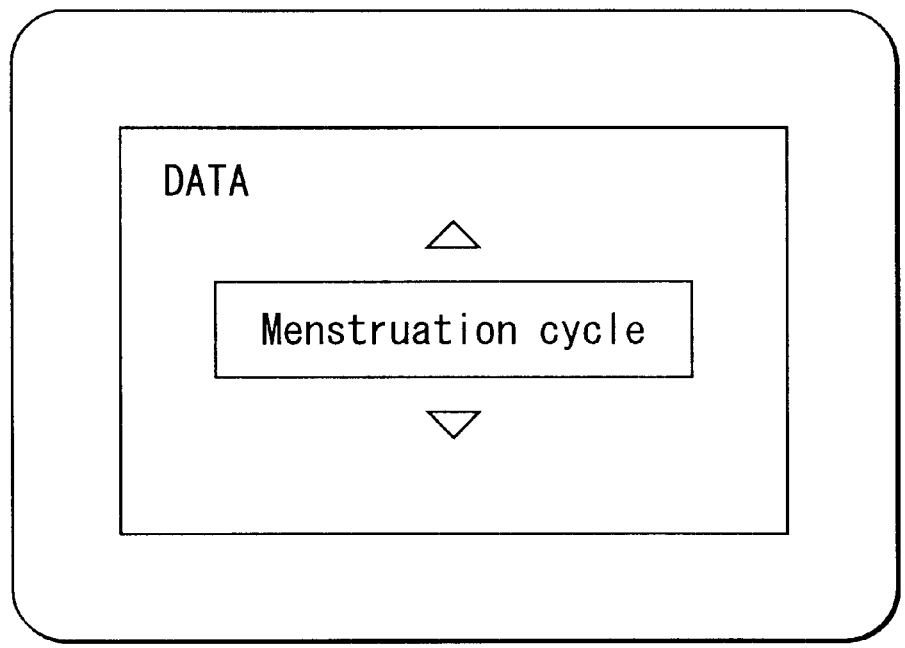
FIG. 62 shows a selected item in the display.
Figure 63:
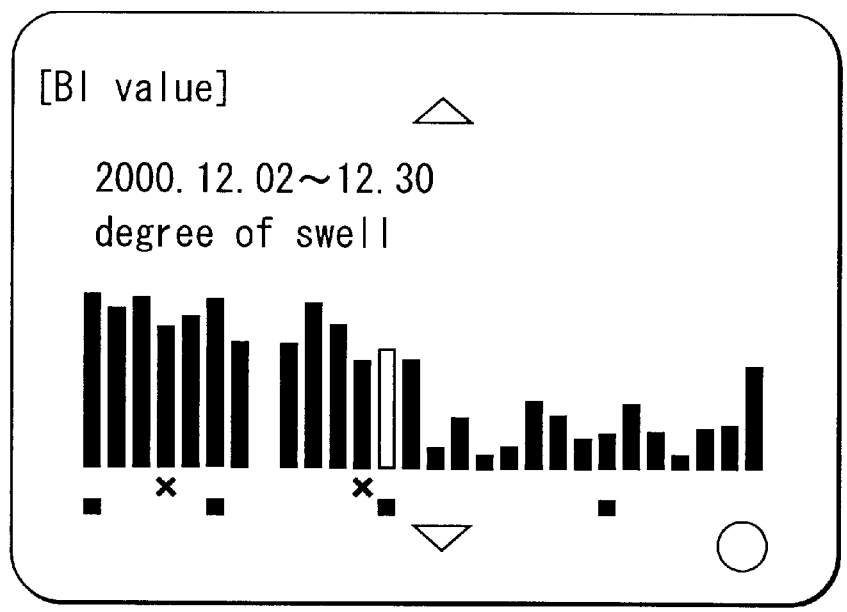
FIG. 63 shows a monthly graphic presentation of BI values.
Figure 64:
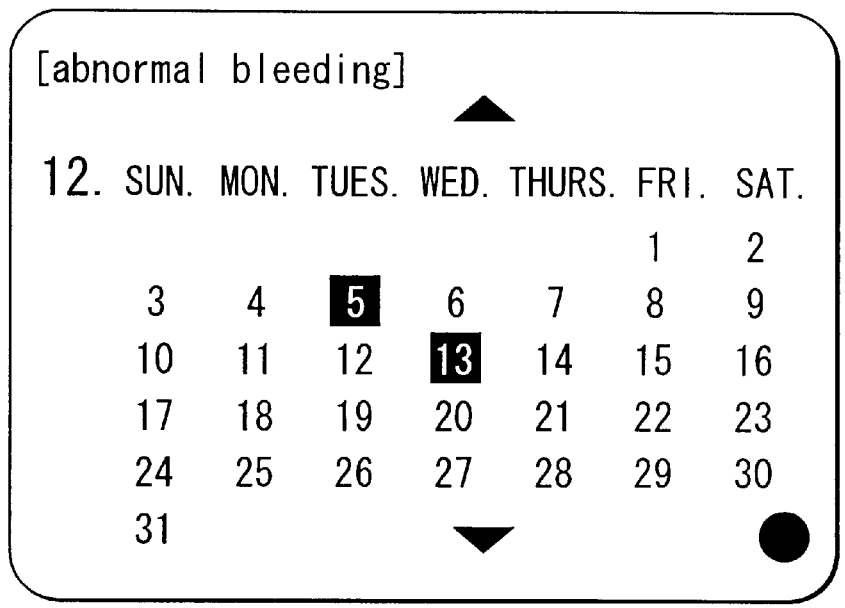
FIG. 64 shows an image of calendar page indicating the days on which the woman experienced abnormal bleedings.

Referring to FIG. 50, the DATA mode processing is described. In the DATA mode a graphic representation of specified data and a particular day are indicated as selected. At STEP S281 the screen shows an item selected (see FIG. 62). At STEP S282 the user uses the ↑ or ↓ button sector to allow "Weight Graph", "BI Graph", "Abnormal Bleeding Day", "Intimate Physical Contact Day", "Menstruation Cycle" and other items to move on the screen up or down so that the user can read it for selection. When a required selection is made, the decision button 41 is depressed. At Step S283 the contents of the selected item are given as for instance, follows: a graph is shown when the selected item is "Graph". Specifically in response to selection of the "BI Graph" there appears a bar graph showing how the BI value varies each and every day (see FIG. 63). Thus, the user can realize how BI values vary with her physical condition, and which stage her physical condition has reached. When "Day" is selected as the item, there appears a calendar page which includes the particular day in reversed condition. In a case where "Abnormal Bleeding Day" is selected as the item, the screen of FIG. 64 appears in the display. The selected particular days are indicated in the calendar page. Alternatively the date may be given in the form of letters and numbers. The → button sector is depressed, or otherwise, a predetermined length of time has passed, and then, the proceeding returns to Step S281. When the cancel button 41*h* is depressed, the proceeding returns to STEP S3.

Figure 51:
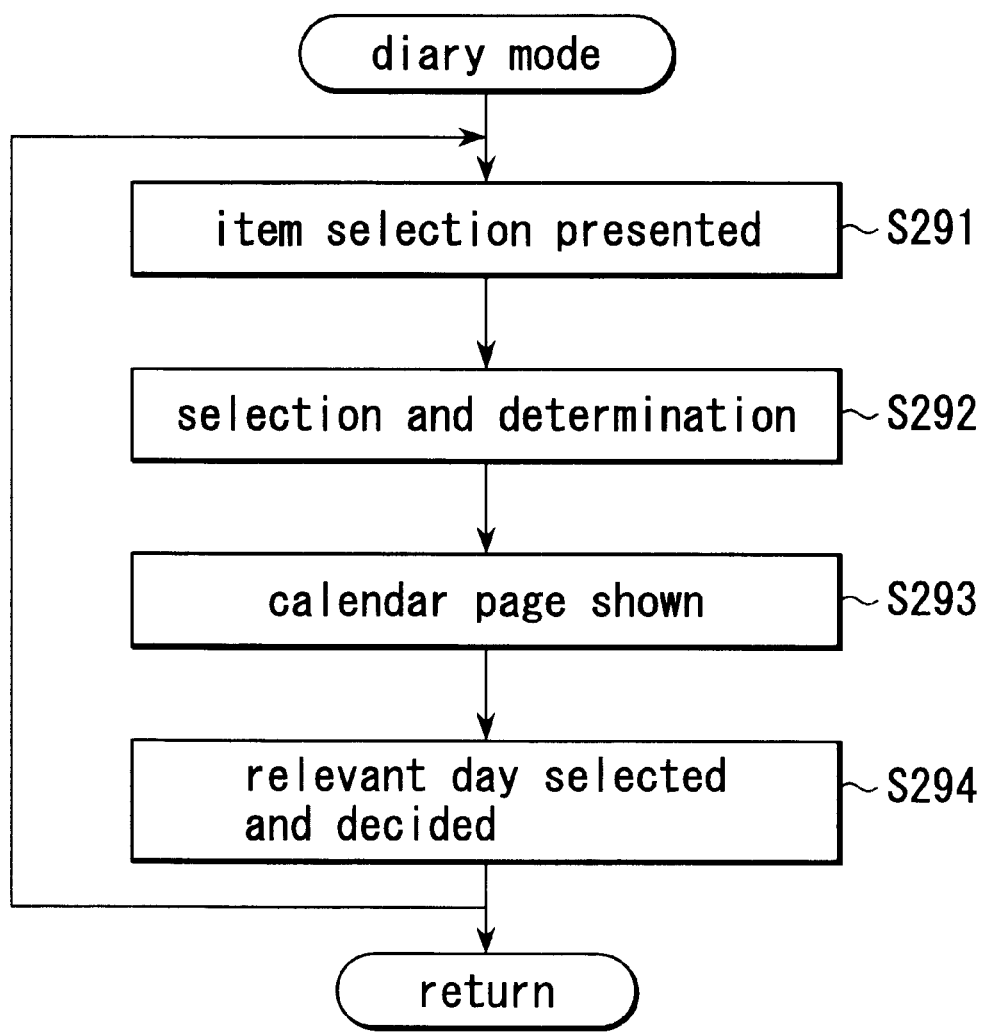
FIG. 51 shows a series of steps in the diary mode.

Referring to FIG. 51, the DIARY mode processing is described. In the DIARY mode a certain day or days can be indicated or the indicated day or days can be corrected. At STEP S291 there appears an item selection screen as in FIG. 62. At STEP S292 the user uses the ↑ or ↓ button sector to allow "Abnormal Bleeding Day", "Beginning Day of the Menstruation", "Intimate Physical Contact Day" and other items to move on the screen up or down so that the user can read it for selection. At Step S293 a selected calendar page is given (see FIG. 64). At Step 294 the user uses the ↓, ↑, ← or → button sector to move and put the cursor on the relevant day for selection, and can decide the day when the decision button 41*f* is depressed. Then, the proceeding returns to STEP S291.

Presentation of measurement in the display is so dynamic that the viewer may not feel bored while the measurement is being made. As may be understood the above, the female physical condition managing apparatus according the present invention displays the decided physical condition on the BI transition symbolic curve. This permits the user to realize quickly what stage has been reached in the monthly physical condition. Therefore, the user can catch the transition of the physical condition as one cycle visually.

What is claimed is:

1. A female physical condition managing apparatus comprising:
   a plurality of pairs of electrodes which can be applied to selected points of an outer layer of the skin of a female body;
   a bioelectric impedance meter for determining the value of bioelectric impedance (BI) appearing between one of said pairs of electrodes;
   a memory for storing the so determined BI value;
   a decision-making unit for making a decision about the monthly physical condition of the female on the basis of a time series analysis of the variation of the BI values; and
   a display for showing said decision on the monthly physical condition of the female and a BI transition symbolic curve
   wherein the display has a given mark moving on the BI transition symbolic curve while the required measurement is being effected or while the required decision is being made.

2. A female physical condition managing apparatus according to claim 1 wherein the period of BI transition symbolic curve spans from the menstruation to the next menstruation.

3. A female physical condition managing apparatus according to claim 1 or 2 wherein the monthly physical condition includes at least the delicate period, dieting period, pre- and post-ovulation, PMS preventing period, PMS period or subsequent delicate period.

4. A female physical condition managing apparatus according to claim 1 or 2 wherein the display shows at least one of the degree of swell measured, the date of the physical condition decided and the weight measured at the time the required measurement was determined.

5. A female physical condition managing apparatus according to claim 1 wherein the display shows, in synchronism with the movement of the mark, the name identifying the period of physical condition and/or a swell-symbolic shape illustrating the degree of swell.

6. A female physical condition managing apparatus comprising:
   a plurality of pairs of electrodes which can be applied to selected points of an outer layer of the skin of a female body;
   a bioelectrical impedance meter for determining the value of bioelectrical impedance (BI) appearing between one of said pairs of electrodes;
   a memory for storing the so determined BI value;
   a decision-making unit for making a decision about the monthly physical condition of the female on the basis of a time series analysis of the variation of the BI values; and a display for displaying a given mark moving on a monthly periodic chart while the required measurement is being effected or while the required decision is being made.

7. A female physical condition managing apparatus according to claim 6 wherein the monthly periodic chart is a sinusoidal curve, a circle or a straight line.

8. A female physical condition managing apparatus according to claim 6 or 7 wherein the mark is a circle or an animal figure.

9. A female physical condition managing apparatus according to claim 6 or 7 wherein the mark varies every month and/or every day in shape and/or color.

10. A female physical condition managing apparatus according to claim 6 wherein the display is capable of retrieving selected data of measurement from an associated memory and of showing such data by means of telop while the required measurement is being effected or while the required decision is being made.

11. A female physical condition managing apparatus comprising:

a plurality of pairs of electrodes which can be applied to selected points of an outer layer of the skin of a female body;

a bioelectrical impledance meter for determining the value of bioelectric impedance (BI) appearing between one of said pairs of electrodes;

a memory for storing the so determined BI value;

a decision-making unit for making a decision about the monthly physical condition of the female on the basis of a time series analysis of the variation of the BI values; and a display for displaying an animation-like presentation of monthly period while the required measurement is being effected or while the required decision is being made.

12. A female physical condition managing apparatus according to claim 11 wherein the animation-like presentation of monthly period is composed of a series of figures illustrating how a chick appears from an egg.

13. A female physical condition managing apparatus according to claim 11 wherein the animation-like presentation of monthly period is composed of a series of figures illustrating how the moon varies from crescent to full moon.

* * * * *